(12) United States Patent
Meyer et al.

(10) Patent No.: US 10,874,787 B2
(45) Date of Patent: Dec. 29, 2020

(54) DEGASSING SYSTEM FOR DIALYSIS

(71) Applicant: Medtronic, Inc., Minneapolis, MN (US)

(72) Inventors: Thomas E. Meyer, Stillwater, MN (US); Samuel J. Schmidt, Duluth, MN (US); William P. Hajko, Safety Harbor, FL (US); Carl Wilbert Gomes, II, Parrish, FL (US)

(73) Assignee: Medtronic, Inc., Minneapolis, MN (US)

(*) Notice: Subject to any disclaimer, the term of this patent is extended or adjusted under 35 U.S.C. 154(b) by 161 days.

(21) Appl. No.: 15/885,738

(22) Filed: Jan. 31, 2018

(65) Prior Publication Data
US 2018/0243494 A1   Aug. 30, 2018

Related U.S. Application Data

(63) Continuation of application No. 15/618,187, filed on Jun. 9, 2017, now Pat. No. 10,420,872, and a (Continued)

(51) Int. Cl.
*A61M 1/16*   (2006.01)
*B01D 19/00*   (2006.01)

(52) U.S. Cl.
CPC ........ *A61M 1/1658* (2013.01); *A61M 1/1696* (2013.01); *B01D 19/0036* (2013.01); *B01D 19/0047* (2013.01); *B01D 19/0063* (2013.01); *B01D 19/0068* (2013.01); *A61M 2202/0225* (2013.01); *A61M 2205/3382* (2013.01); *A61M 2205/3386* (2013.01)

(58) Field of Classification Search
CPC ............ B01D 19/0031; B01D 19/0036; B01D 19/0047; B01D 19/0063; B01D 19/0068; A61M 1/1658; A61M 1/1696
See application file for complete search history.

(56) References Cited

U.S. PATENT DOCUMENTS 3,091,098 A * 5/1963 Bowers .............. B01D 19/0047
62/180
3,370,710 A 2/1968 Bluemle
(Continued)

FOREIGN PATENT DOCUMENTS

CN   101687070      3/2010
CN   101883594 A    11/2010
(Continued)

OTHER PUBLICATIONS

English language machine translation for FR 2237639. Retrieved from http://translationportal.epo.org on Feb. 27, 2020. (Year: 2020).*
(Continued)

*Primary Examiner* — Jason M Greene
(74) *Attorney, Agent, or Firm* — Hahn & Associates

(57) ABSTRACT

The invention relates to a degassing vessel and related systems and methods that can remove certain gases such as carbon dioxide from a dialysis system with minimal foaming inside the degassing vessel. The invention further relates to mechanical systems and methods for degassing a dialysate or any fluid used for, during or resulting from dialysis.

8 Claims, 13 Drawing Sheets

Related U.S. Application Data continuation-in-part of application No. 14/566,686, filed on Dec. 10, 2014, now Pat. No. 9,713,665, which is a continuation of application No. 14/566,686, filed on Dec. 10, 2014, now Pat. No. 9,713,665.

(56) References Cited

U.S. PATENT DOCUMENTS

| | | |
|---|---|---|
| 3,506,126 A | 4/1970 | Lindsay, Jr. |
| 3,608,729 A | 9/1971 | Haselden |
| 3,669,878 A | 6/1972 | Marantz |
| 3,669,880 A | 6/1972 | Marantz |
| 3,692,648 A | 9/1972 | Matloff |
| 3,776,819 A | 12/1973 | Williams |
| 3,809,241 A | 5/1974 | Alvine |
| 3,850,835 A | 11/1974 | Marantz |
| 3,884,808 A | 5/1975 | Scott |
| 3,902,490 A | 9/1975 | Jacobsen |
| 3,932,150 A | 1/1976 | Komai |
| 3,939,069 A | 2/1976 | Granger |
| 3,989,622 A | 11/1976 | Marantz |
| 4,060,485 A | 11/1977 | Eaton |
| 4,094,775 A | 6/1978 | Mueller |
| 4,136,708 A | 1/1979 | Cosentino |
| 4,142,845 A | 3/1979 | Lepp |
| 4,201,555 A | 5/1980 | Tkach |
| 4,209,392 A | 6/1980 | Wallace |
| 4,269,708 A | 5/1981 | Bonomini |
| 4,316,725 A | 2/1982 | Hovind |
| 4,371,385 A | 2/1983 | Johnson |
| 4,374,382 A | 2/1983 | Markowitz |
| 4,376,707 A | 3/1983 | Lehmann |
| 4,381,999 A | 5/1983 | Boucher |
| 4,430,098 A | 2/1984 | Bowman |
| 4,460,555 A | 7/1984 | Thompson |
| 4,490,135 A | 12/1984 | Troutner |
| 4,556,063 A | 12/1985 | Thompson |
| 4,562,751 A | 1/1986 | Nason |
| 4,581,141 A | 4/1986 | Ash |
| 4,612,122 A | 9/1986 | Ambrus |
| 4,650,587 A | 3/1987 | Polak |
| 4,678,408 A | 7/1987 | Mason |
| 4,685,903 A | 8/1987 | Cable |
| 4,695,385 A | 9/1987 | Boag |
| 4,715,398 A | 12/1987 | Shouldice |
| 4,744,808 A * | 5/1988 | Treu ............... B01D 19/0063 137/412 |
| 4,747,822 A | 5/1988 | Peabody |
| 4,750,494 A | 6/1988 | King |
| 4,816,162 A | 3/1989 | Rosskopf et al. |
| 4,826,663 A | 5/1989 | Alberti |
| 4,828,693 A | 5/1989 | Lindsay |
| 4,885,001 A | 12/1989 | Leppert |
| 4,900,308 A | 2/1990 | Verkaart |
| 4,915,713 A | 4/1990 | Buzza |
| 4,950,230 A | 8/1990 | Kendell |
| 4,952,509 A * | 8/1990 | Wegner ............. B01D 19/0047 435/301.1 |
| 4,977,888 A | 12/1990 | Rietter |
| 5,015,388 A | 5/1991 | Pusineri |
| 5,032,265 A | 7/1991 | Jha |
| 5,067,446 A * | 11/1991 | Blangetti .......... B01D 19/0047 122/32 |
| 5,080,653 A | 1/1992 | Voss |
| 5,092,886 A | 3/1992 | Dobos-Hardy |
| 5,097,122 A | 3/1992 | Coiman |
| 5,114,580 A | 5/1992 | Ahmad |
| 5,127,404 A | 7/1992 | Wyborny |
| 5,141,493 A | 8/1992 | Jacobsen |
| 5,180,403 A * | 1/1993 | Kogure ............. B01D 19/0047 95/265 |
| 5,192,132 A | 3/1993 | Pelensky |
| 5,203,890 A | 4/1993 | Tatsuo |
| 5,230,702 A | 7/1993 | Lindsay |
| 5,284,470 A | 2/1994 | Beltz |
| 5,302,288 A | 4/1994 | Meidl |
| 5,305,745 A | 4/1994 | Zacouto |
| 5,308,315 A | 5/1994 | Khuri |
| 5,318,750 A | 6/1994 | Lascombes |
| 5,399,157 A | 3/1995 | Goux |
| 5,419,347 A | 5/1995 | Carruth |
| 5,441,049 A | 8/1995 | Masano |
| 5,442,969 A | 8/1995 | Troutner |
| 5,468,388 A | 11/1995 | Goddard |
| 5,507,723 A | 4/1996 | Keshaviah |
| 5,591,344 A | 1/1997 | Kenley |
| 5,643,201 A | 7/1997 | Peabody |
| 5,662,806 A | 9/1997 | Keshaviah et al. |
| 5,683,432 A | 11/1997 | Goedeke |
| 5,685,835 A | 11/1997 | Brugger |
| 5,685,988 A | 11/1997 | Malchesky |
| 5,702,536 A | 12/1997 | Carruth |
| 5,744,031 A | 4/1998 | Bene |
| 5,762,782 A | 6/1998 | Kenley |
| 5,849,179 A | 12/1998 | Emerson |
| 5,858,186 A | 1/1999 | Glass |
| 5,863,421 A | 1/1999 | Peter |
| 5,938,938 A | 8/1999 | Bosetto |
| 5,944,684 A | 8/1999 | Roberts |
| 5,948,251 A | 9/1999 | Brugger |
| 6,048,732 A | 4/2000 | Anslyn |
| 6,052,622 A | 4/2000 | Holmstrom |
| 6,058,331 A | 5/2000 | King |
| 6,114,176 A | 9/2000 | Edgson et al. |
| 6,126,831 A | 10/2000 | Goldau |
| 6,171,480 B1 | 1/2001 | Lee |
| 6,230,059 B1 | 5/2001 | Duffin |
| 6,248,093 B1 | 6/2001 | Moberg |
| 6,251,167 B1 * | 6/2001 | Berson ............... B01D 19/0047 210/188 |
| 6,254,567 B1 | 7/2001 | Treu |
| 6,264,680 B1 | 7/2001 | Ash |
| 6,321,101 B1 | 11/2001 | Holmstrom |
| 6,362,591 B1 | 3/2002 | Moberg |
| 6,363,279 B1 | 3/2002 | Ben-Haim |
| 6,521,184 B1 | 2/2003 | Edgson et al. |
| 6,554,798 B1 | 4/2003 | Mann |
| 6,555,986 B2 | 4/2003 | Moberg |
| 6,589,229 B1 | 7/2003 | Connelly |
| 6,593,747 B2 | 7/2003 | Puskas |
| 6,602,399 B1 | 8/2003 | Fromherz |
| 6,627,164 B1 | 9/2003 | Wong |
| 6,666,840 B1 | 12/2003 | Falkvall et al. |
| 6,676,608 B1 | 1/2004 | Keren |
| 6,711,439 B1 | 3/2004 | Bradley |
| 6,719,745 B1 | 4/2004 | Taylor |
| 6,726,647 B1 | 4/2004 | Sternby |
| 6,780,322 B1 | 8/2004 | Bissler |
| 6,814,724 B2 | 11/2004 | Taylor |
| 6,818,196 B2 | 11/2004 | Wong |
| 6,824,524 B1 | 11/2004 | Favre |
| 6,861,266 B1 | 3/2005 | Sternby |
| 6,878,283 B2 | 4/2005 | Thompson |
| 6,960,179 B2 | 11/2005 | Gura |
| 7,023,359 B2 | 4/2006 | Goetz |
| 7,033,498 B2 | 4/2006 | Wong |
| 7,074,332 B2 | 7/2006 | Summerton |
| 7,077,819 B1 | 7/2006 | Goldau |
| 7,097,630 B2 | 8/2006 | Gotch |
| 7,101,519 B2 | 9/2006 | Wong |
| 7,153,693 B2 | 12/2006 | Tajiri |
| 7,169,303 B2 | 1/2007 | Sullivan |
| 7,208,092 B2 | 4/2007 | Micheli |
| 7,241,272 B2 | 7/2007 | Karoor |
| 7,276,042 B2 | 10/2007 | Polaschegg |
| 7,279,031 B1 | 10/2007 | Wright |
| 7,318,892 B2 | 1/2008 | Connell |
| 7,326,576 B2 | 2/2008 | Womble et al. |
| 7,435,342 B2 | 10/2008 | Tsukamoto |
| 7,488,447 B2 | 2/2009 | Sternby |
| 7,500,958 B2 | 3/2009 | Asbrink |
| 7,537,688 B2 | 5/2009 | Tarumi |
| 7,544,300 B2 | 6/2009 | Brugger |
| 7,544,737 B2 | 6/2009 | Poss |

(56) References Cited

U.S. PATENT DOCUMENTS

| | | |
|---|---|---|
| 7,563,240 B2 | 7/2009 | Gross |
| 7,566,432 B2 | 7/2009 | Wong |
| 7,575,564 B2 | 8/2009 | Childers |
| 7,597,806 B2 | 10/2009 | Uchi |
| 7,674,231 B2 | 3/2010 | McCombie |
| 7,704,361 B2 | 4/2010 | Garde |
| 7,736,507 B2 | 6/2010 | Wong |
| 7,744,553 B2 | 6/2010 | Kelly |
| 7,754,852 B2 | 7/2010 | Burnett |
| 7,756,572 B1 | 7/2010 | Fard |
| 7,776,210 B2 | 8/2010 | Rosenbaum |
| 7,785,463 B2 | 8/2010 | Bissler |
| 7,790,103 B2 | 9/2010 | Shah |
| 7,794,141 B2 | 9/2010 | Perry |
| 7,794,419 B2 | 9/2010 | Paolini |
| 7,850,635 B2 | 12/2010 | Polaschegg |
| 7,857,976 B2 | 12/2010 | Bissler |
| 7,867,214 B2 | 1/2011 | Childers |
| 7,896,831 B2 | 3/2011 | Sternby |
| 7,922,686 B2 | 4/2011 | Childers |
| 7,922,911 B2 | 4/2011 | Micheli |
| 7,947,179 B2 | 5/2011 | Rosenbaum |
| 7,955,290 B2 | 6/2011 | Karoor |
| 7,955,291 B2 | 6/2011 | Sternby |
| 7,967,022 B2 | 6/2011 | Grant |
| 7,981,082 B2 | 7/2011 | Wang |
| 7,988,854 B2 | 8/2011 | Tsukamoto |
| 8,002,726 B2 | 8/2011 | Karoor |
| 8,029,454 B2 | 10/2011 | Kelly |
| 8,034,161 B2 | 10/2011 | Gura |
| 8,066,658 B2 | 11/2011 | Karoor |
| 8,070,709 B2 | 12/2011 | Childers |
| 8,080,161 B2 | 12/2011 | Baxter Int |
| 8,087,303 B2 | 1/2012 | Beavis |
| 8,096,969 B2 | 1/2012 | Roberts |
| 8,180,574 B2 | 5/2012 | Lo |
| 8,183,046 B2 | 5/2012 | Lu |
| 8,187,250 B2 | 5/2012 | Roberts |
| 8,197,439 B2 | 6/2012 | Wang |
| 8,202,241 B2 | 6/2012 | Karakama |
| 8,246,826 B2 | 8/2012 | Wilt |
| 8,273,049 B2 | 9/2012 | Demers |
| 8,292,594 B2 | 10/2012 | Tracey |
| 8,303,532 B2 | 11/2012 | Hamada |
| 8,313,642 B2 | 11/2012 | Yu |
| 8,317,492 B2 | 11/2012 | Demers |
| 8,357,113 B2 | 1/2013 | Childers |
| 8,366,316 B2 | 2/2013 | Kamen |
| 8,366,655 B2 | 2/2013 | Kamen |
| 8,404,491 B2 | 3/2013 | Li |
| 8,409,441 B2 | 4/2013 | Wilt |
| 8,409,444 B2 | 4/2013 | Wong |
| 8,449,487 B2 * | 5/2013 | Hovland ............ A61M 1/1658 604/5.01 |
| 8,491,517 B2 | 7/2013 | Karoor |
| 8,496,809 B2 | 7/2013 | Roger |
| 8,499,780 B2 | 8/2013 | Wilt |
| 8,500,672 B2 | 8/2013 | Caleffi |
| 8,500,676 B2 | 8/2013 | Jansson |
| 8,500,994 B2 | 8/2013 | Weaver |
| 8,512,271 B2 | 8/2013 | Moissl |
| 8,518,258 B2 | 8/2013 | Balschat |
| 8,518,260 B2 | 8/2013 | Raimann |
| 8,521,482 B2 | 8/2013 | Akonur |
| 8,535,525 B2 | 9/2013 | Heyes |
| 8,560,510 B2 | 10/2013 | Brueggerhoff |
| 8,562,822 B2 | 10/2013 | Roger |
| 8,580,112 B2 | 11/2013 | Updyke |
| 8,597,227 B2 | 12/2013 | Childers |
| 8,696,626 B2 | 4/2014 | Kirsch |
| 8,777,892 B2 | 7/2014 | Sandford |
| 8,903,492 B2 | 12/2014 | Soykan |
| 8,906,240 B2 | 12/2014 | Crnkovich |
| 9,144,640 B2 | 9/2015 | Pudil |
| 9,173,987 B2 | 11/2015 | Meyer |
| 10,297,593 B2 | 5/2019 | Gejo |
| 2002/0027106 A1 | 3/2002 | Smith |
| 2002/0042561 A1 | 4/2002 | Schulman |
| 2002/0045851 A1 | 4/2002 | Suzuki |
| 2002/0104800 A1 | 8/2002 | Collins |
| 2002/0112609 A1 | 8/2002 | Wong |
| 2003/0010717 A1 | 1/2003 | Brugger |
| 2003/0034305 A1 | 2/2003 | Luehmann |
| 2003/0080059 A1 | 5/2003 | Peterson |
| 2003/0097086 A1 | 5/2003 | Gura |
| 2003/0105424 A1 | 6/2003 | Karoor |
| 2003/0105435 A1 | 6/2003 | Taylor |
| 2003/0114787 A1 | 6/2003 | Gura |
| 2004/0019312 A1 * | 1/2004 | Childers ............ A61M 1/1656 604/4.01 |
| 2004/0019320 A1 | 1/2004 | Childers |
| 2004/0068219 A1 | 4/2004 | Summerton |
| 2004/0082903 A1 | 4/2004 | Micheli |
| 2004/0099593 A1 | 5/2004 | DePaolis |
| 2004/0102732 A1 | 5/2004 | Naghavi |
| 2004/0143173 A1 | 7/2004 | Reghabi |
| 2004/0147900 A1 | 7/2004 | Polaschegg |
| 2004/0168969 A1 | 9/2004 | Sternby |
| 2004/0215090 A1 | 10/2004 | Erkkila |
| 2005/0006296 A1 | 1/2005 | Sullivan |
| 2005/0065760 A1 | 3/2005 | Murtfeldt |
| 2005/0101901 A1 | 5/2005 | Gura |
| 2005/0113796 A1 | 5/2005 | Taylor |
| 2005/0115898 A1 | 6/2005 | Sternby |
| 2005/0126961 A1 | 6/2005 | Bissler |
| 2005/0131331 A1 | 6/2005 | Kelly |
| 2005/0131332 A1 | 6/2005 | Kelly |
| 2005/0153904 A1 | 6/2005 | Fager |
| 2005/0126998 A1 | 7/2005 | Childers |
| 2005/0148923 A1 | 7/2005 | Sternby |
| 2005/0150832 A1 | 7/2005 | Tsukamoto |
| 2005/0234381 A1 | 10/2005 | Niemetz |
| 2005/0274658 A1 | 12/2005 | Rosenbaum |
| 2006/0025661 A1 | 2/2006 | Sweeney |
| 2006/0217771 A1 | 2/2006 | Soykan |
| 2006/0054489 A1 | 3/2006 | Denes |
| 2006/0076295 A1 | 4/2006 | Leonard |
| 2006/0157335 A1 | 7/2006 | Levine |
| 2006/0157413 A1 | 7/2006 | Bene |
| 2006/0186044 A1 | 8/2006 | Nalesso |
| 2006/0195064 A1 | 8/2006 | Plahey |
| 2006/0226079 A1 | 10/2006 | Mori |
| 2006/0241709 A1 | 10/2006 | Soykan |
| 2006/0264894 A1 | 11/2006 | Moberg |
| 2007/0007208 A1 | 1/2007 | Brugger |
| 2007/0066928 A1 | 3/2007 | Lannoy |
| 2007/0072285 A1 | 3/2007 | Barringer |
| 2007/0138011 A1 | 6/2007 | Hofmann |
| 2007/0140916 A1 | 6/2007 | Spiss |
| 2007/0175827 A1 | 8/2007 | Wariar |
| 2007/0179431 A1 | 8/2007 | Roberts |
| 2007/0213653 A1 | 9/2007 | Childers |
| 2007/0213665 A1 | 9/2007 | Curtin |
| 2007/0215545 A1 | 9/2007 | Bissler |
| 2007/0243113 A1 | 10/2007 | DiLeo |
| 2007/0255250 A1 | 11/2007 | Moberg |
| 2008/0006570 A1 | 1/2008 | Gura |
| 2008/0015493 A1 | 1/2008 | Childers et al. |
| 2008/0021337 A1 | 1/2008 | Li |
| 2008/0051696 A1 | 2/2008 | Curtin |
| 2008/0053905 A9 | 3/2008 | Brugger |
| 2008/0067132 A1 | 3/2008 | Ross |
| 2008/0093276 A1 | 4/2008 | Roger |
| 2008/0154543 A1 | 6/2008 | Rajagopal |
| 2008/0215247 A1 | 9/2008 | Tonelli |
| 2008/0217245 A1 | 9/2008 | Rambod |
| 2008/0230473 A1 | 9/2008 | Herbst |
| 2008/0253427 A1 | 10/2008 | Kamen |
| 2009/0012450 A1 | 1/2009 | Shah |
| 2009/0020471 A1 | 1/2009 | Tsukamoto |
| 2009/0078636 A1 | 3/2009 | Uchi |
| 2009/0084199 A1 | 4/2009 | Wright |
| 2009/0084718 A1 | 4/2009 | Prisco |
| 2009/0084721 A1 | 4/2009 | Yardimci |

(56) References Cited

U.S. PATENT DOCUMENTS

| | | |
|---|---|---|
| 2009/0101549 A1 | 4/2009 | Kamen |
| 2009/0101552 A1 | 4/2009 | Fulkerson |
| 2009/0101577 A1 | 4/2009 | Fulkerson |
| 2009/0105629 A1 | 4/2009 | Grant |
| 2009/0107335 A1 | 4/2009 | Wilt |
| 2009/0124963 A1 | 5/2009 | Hogard |
| 2009/0127193 A1 | 5/2009 | Updyke |
| 2009/0131858 A1 | 5/2009 | Fissell |
| 2009/0159527 A1 | 6/2009 | Mickols |
| 2009/0171261 A1 | 7/2009 | Sternby |
| 2009/0173682 A1 | 7/2009 | Robinson |
| 2009/0182263 A1 | 7/2009 | Burbank |
| 2009/0187138 A1 | 7/2009 | Lundtveit |
| 2009/0216045 A1 | 8/2009 | Singh |
| 2009/0223539 A1 | 9/2009 | Gibbel |
| 2009/0275849 A1 | 11/2009 | Stewart |
| 2009/0275883 A1 | 11/2009 | Chapman |
| 2009/0281484 A1 | 11/2009 | Childers |
| 2009/0282980 A1 | 11/2009 | Gura |
| 2009/0314063 A1 | 12/2009 | Sternby |
| 2010/0004588 A1 | 1/2010 | Yeh |
| 2010/0007838 A1 | 1/2010 | Fujimoto |
| 2010/0010429 A1 | 1/2010 | Childers |
| 2010/0022936 A1 | 1/2010 | Gura |
| 2010/0030151 A1 | 2/2010 | Kirsch |
| 2010/0042035 A1 | 2/2010 | Moissl |
| 2010/0051552 A1 | 3/2010 | Rohde |
| 2010/0078092 A1 | 4/2010 | Weilhoefer |
| 2010/0078381 A1 | 4/2010 | Merchant |
| 2010/0078387 A1 | 4/2010 | Wong |
| 2010/0084330 A1 | 4/2010 | Wong |
| 2010/0087771 A1 | 4/2010 | Karakama |
| 2010/0094158 A1 | 4/2010 | Solem |
| 2010/0100027 A1* | 4/2010 | Schilthuizen ....... A61M 1/3486 604/6.09 |
| 2010/0102190 A1 | 4/2010 | Zhu et al. |
| 2010/0106071 A1 | 4/2010 | Wallenborg |
| 2010/0114012 A1* | 5/2010 | Sandford ............ A61M 1/1694 604/28 |
| 2010/0130906 A1 | 5/2010 | Balschat |
| 2010/0137693 A1 | 6/2010 | Porras |
| 2010/0137782 A1 | 6/2010 | Jansson |
| 2010/0140149 A1 | 6/2010 | Fulkerson |
| 2010/0168546 A1 | 7/2010 | Kamath |
| 2010/0192686 A1 | 8/2010 | Kamen |
| 2010/0199670 A1 | 8/2010 | Robertson |
| 2010/0213127 A1 | 8/2010 | Castellarnau |
| 2010/0217180 A1 | 8/2010 | Akonur |
| 2010/0217181 A1 | 8/2010 | Roberts |
| 2010/0224492 A1 | 9/2010 | Ding |
| 2010/0234795 A1 | 9/2010 | Wallenas |
| 2010/0241045 A1 | 9/2010 | Kelly |
| 2010/0252490 A1 | 10/2010 | Fulkerson |
| 2010/0274171 A1 | 10/2010 | Caleffi |
| 2010/0282662 A1 | 11/2010 | Lee |
| 2010/0312172 A1 | 12/2010 | Hoffman |
| 2010/0312174 A1 | 12/2010 | Hoffman |
| 2010/0326911 A1 | 12/2010 | Rosenbaum |
| 2010/0327586 A1 | 12/2010 | Mardirossian |
| 2011/0009798 A1 | 1/2011 | Kelly |
| 2011/0017665 A1 | 1/2011 | Updyke |
| 2011/0048949 A1 | 3/2011 | Ding et al. |
| 2011/0066043 A1 | 3/2011 | Banet |
| 2011/0071465 A1 | 3/2011 | Wang |
| 2011/0077574 A1 | 3/2011 | Sigg |
| 2011/0079558 A1 | 4/2011 | Raimann |
| 2011/0087187 A1 | 4/2011 | Beck |
| 2011/0100909 A1 | 5/2011 | Stange |
| 2011/0105983 A1 | 5/2011 | Kelly |
| 2011/0106003 A1 | 5/2011 | Childers |
| 2011/0120930 A1 | 5/2011 | Mishkin |
| 2011/0120946 A1 | 5/2011 | Levin |
| 2011/0130666 A1 | 6/2011 | Dong |
| 2011/0132838 A1 | 6/2011 | Curtis |
| 2011/0144570 A1 | 6/2011 | Childers |
| 2011/0160637 A1 | 6/2011 | Beiriger |
| 2011/0163030 A1 | 7/2011 | Weaver |
| 2011/0163034 A1 | 7/2011 | Castellarnau |
| 2011/0168017 A1 | 7/2011 | Lamers |
| 2011/0184340 A1 | 7/2011 | Tan |
| 2011/0189048 A1 | 8/2011 | Curtis |
| 2011/0220562 A1 | 9/2011 | Beiriger |
| 2011/0247973 A1 | 10/2011 | Sargand |
| 2011/0272337 A1 | 11/2011 | Palmer |
| 2011/0284377 A1 | 11/2011 | Rohde |
| 2011/0315611 A1 | 12/2011 | Fulkerson |
| 2011/0315632 A1 | 12/2011 | Freije |
| 2012/0006762 A1* | 1/2012 | McCabe ............ B01D 19/0036 210/801 |
| 2012/0016228 A1 | 1/2012 | Kroh |
| 2012/0031825 A1 | 2/2012 | Gura |
| 2012/0083729 A1 | 4/2012 | Childers |
| 2012/0085707 A1 | 4/2012 | Beiriger |
| 2012/0092025 A1 | 4/2012 | Volker |
| 2012/0115248 A1 | 5/2012 | Ansyln |
| 2012/0199205 A1 | 8/2012 | Eyrard |
| 2012/0220528 A1 | 8/2012 | Vanantwerp |
| 2012/0220926 A1 | 8/2012 | Soykan |
| 2012/0248017 A1 | 10/2012 | Beiriger |
| 2012/0258545 A1 | 10/2012 | Ash |
| 2012/0258546 A1 | 10/2012 | Marran |
| 2012/0259276 A1 | 10/2012 | Childers |
| 2012/0273354 A1 | 11/2012 | Orhan et al. |
| 2012/0273415 A1 | 11/2012 | Gerber |
| 2012/0273420 A1 | 11/2012 | Gerber |
| 2012/0277546 A1 | 11/2012 | Soykan |
| 2012/0277552 A1 | 11/2012 | Gerber |
| 2012/0277604 A1 | 11/2012 | Gerber |
| 2012/0277650 A1 | 11/2012 | Gerber |
| 2012/0277655 A1 | 11/2012 | Gerber |
| 2012/0277722 A1 | 11/2012 | Gerber |
| 2012/0302945 A1 | 11/2012 | Hedmann |
| 2013/0001165 A1 | 1/2013 | Pohlmeier |
| 2013/0015302 A1 | 1/2013 | Gkhan |
| 2013/0018301 A1 | 1/2013 | Weaver |
| 2013/0019994 A1 | 1/2013 | Schaer |
| 2013/0030356 A1 | 1/2013 | Ding |
| 2013/0037465 A1 | 2/2013 | Heyes |
| 2013/0062265 A1 | 3/2013 | Balschat |
| 2013/0193073 A1 | 8/2013 | Hogard |
| 2013/0199998 A1 | 8/2013 | Kelly |
| 2013/0211730 A1 | 8/2013 | Wolff |
| 2013/0213890 A1 | 8/2013 | Kelly |
| 2013/0228516 A1 | 9/2013 | Jonsson |
| 2013/0228517 A1 | 9/2013 | Roger |
| 2013/0231607 A1 | 9/2013 | Roger |
| 2013/0248426 A1 | 9/2013 | Pouchoulin |
| 2013/0256227 A1 | 10/2013 | Kelly |
| 2013/0274642 A1 | 10/2013 | Soykan |
| 2013/0304020 A1 | 11/2013 | Wilt |
| 2013/0324915 A1 | 12/2013 | (Krensky) Britton |
| 2013/0330208 A1 | 12/2013 | Ly |
| 2013/0331774 A1 | 12/2013 | Farrell |
| 2014/0001112 A1 | 1/2014 | Karoor |
| 2014/0018727 A1 | 1/2014 | Burbank |
| 2014/0018728 A1 | 1/2014 | Plahey |
| 2014/0042092 A1 | 2/2014 | Akonur |
| 2014/0065950 A1 | 3/2014 | Mendelsohn |
| 2014/0088442 A1 | 3/2014 | Soykan |
| 2014/0110340 A1 | 4/2014 | White |
| 2014/0110341 A1 | 4/2014 | White |
| 2014/0158538 A1 | 6/2014 | Collier |
| 2014/0158588 A1 | 6/2014 | Pudil |
| 2014/0158623 A1 | 6/2014 | Pudil |
| 2014/0190876 A1 | 7/2014 | Meyer |
| 2014/0190885 A1 | 7/2014 | Meyer |
| 2014/0190886 A1 | 7/2014 | Pudil |
| 2014/0190891 A1 | 7/2014 | Lura |
| 2014/0216250 A1 | 8/2014 | Meyer |
| 2014/0217020 A1 | 8/2014 | Meyer |
| 2014/0217027 A1 | 8/2014 | Meyer |
| 2014/0217028 A1 | 8/2014 | Pudil |
| 2014/0217029 A1 | 8/2014 | Meyer |
| 2014/0217030 A1 | 8/2014 | Meyer |

(56) References Cited

U.S. PATENT DOCUMENTS

| | | |
|---|---|---|
| 2014/0220699 A1 | 8/2014 | Pudil |
| 2014/0224736 A1 | 8/2014 | Heide |
| 2014/0251908 A1 | 9/2014 | Ding |
| 2015/0057602 A1 | 2/2015 | Mason |
| 2015/0083647 A1 | 3/2015 | Meyer |
| 2015/0114891 A1 | 4/2015 | Meyer |
| 2015/0144539 A1 | 5/2015 | Pudil |
| 2015/0144542 A1 | 5/2015 | Pudil |
| 2015/0157960 A1 | 6/2015 | Pudil |
| 2015/0238673 A1 | 8/2015 | Gerber |
| 2015/0250937 A1 | 9/2015 | Pudil |
| 2015/0258268 A1 | 9/2015 | Collier |
| 2015/0352270 A1 | 12/2015 | Pudil |
| 2016/0038666 A1 | 2/2016 | Kelly |
| 2016/0166748 A1 | 6/2016 | Meyer |
| 2016/0166751 A1 | 6/2016 | Meyer |
| 2016/0166752 A1 | 6/2016 | Meyer |
| 2016/0166753 A1 | 6/2016 | Meyer |

FOREIGN PATENT DOCUMENTS

| | | | |
|---|---|---|---|
| CN | 102307650 | | 1/2012 |
| CN | 202105667 | | 1/2012 |
| CN | 101237918 | | 1/2013 |
| CN | 101883584 | | 7/2013 |
| CN | 103209721 | | 7/2013 |
| CN | 103889481 | A1 | 6/2014 |
| CN | 103957960 | | 7/2014 |
| CN | 201510761050.6 | | 8/2017 |
| DE | 3215003 | | 4/1985 |
| DE | 60-132606 | | 7/1985 |
| DE | 102011052188 | | 1/2013 |
| EP | 0022370 | A1 | 1/1981 |
| EP | 0187109 | | 7/1986 |
| EP | 266795 | A2 | 11/1987 |
| EP | 0264695 | | 4/1988 |
| EP | 0298587 | | 6/1994 |
| EP | 0743071 | | 11/1996 |
| EP | 1124599 | | 5/2000 |
| EP | 1175238 | | 11/2000 |
| EP | 711182 | B1 | 6/2003 |
| EP | 2308526 | | 10/2003 |
| EP | 1364666 | A1 | 11/2003 |
| EP | 1523347 | | 1/2004 |
| EP | 1523350 | | 1/2004 |
| EP | 0906768 | B1 | 2/2004 |
| EP | 1691863 | | 4/2005 |
| EP | 2116269 | | 2/2008 |
| EP | 1450879 | | 10/2008 |
| EP | 1514562 | | 4/2009 |
| EP | 2219703 | | 5/2009 |
| EP | 1592494 | B1 | 6/2009 |
| EP | 1490129 | | 9/2009 |
| EP | 2100553 | A1 | 9/2009 |
| EP | 2398529 | | 11/2010 |
| EP | 2575827 | A2 | 12/2010 |
| EP | 2100553 | | 8/2011 |
| EP | 2388030 | | 11/2011 |
| EP | 2576453 | A2 | 12/2011 |
| EP | 2701580 | | 11/2012 |
| EP | 2701595 | | 11/2012 |
| EP | 1545652 | B1 | 1/2013 |
| EP | 1345856 | B1 | 3/2013 |
| EP | 2344220 | B1 | 4/2013 |
| EP | 1351756 | | 7/2013 |
| EP | 2190498 | | 7/2013 |
| EP | 1414543 | | 9/2013 |
| EP | 2701596 | | 3/2014 |
| EP | 2740502 | | 6/2014 |
| EP | 1787666 | | 11/2015 |
| FR | 2237639 | * | 2/1975 ............ B01D 19/00 |
| FR | 2237639 | | 2/1977 |
| GB | 2479130 | | 5/2011 |
| JP | 60135064 | | 7/1985 |
| JP | 08504116 | | 5/1996 |
| JP | 2002306904 | | 10/2002 |
| JP | 2006325668 | A | 12/2006 |
| JP | 5099464 | | 10/2012 |
| JP | 2013521862 | | 6/2013 |
| WO | 9532010 | A1 | 11/1995 |
| WO | 1996040313 | | 12/1996 |
| WO | 9937342 | | 7/1999 |
| WO | 9937342 | A1 | 7/1999 |
| WO | 0057935 | | 10/2000 |
| WO | WO2000057935 | A1 | 10/2000 |
| WO | 200066197 | A1 | 11/2000 |
| WO | 2000066197 | | 11/2000 |
| WO | 200170307 | A1 | 9/2001 |
| WO | 2001085295 | A2 | 9/2001 |
| WO | 0185295 | A2 | 11/2001 |
| WO | 2002043859 | | 6/2002 |
| WO | 2003043677 | A2 | 5/2003 |
| WO | 2003043680 | | 5/2003 |
| WO | 2003051422 | A2 | 6/2003 |
| WO | 2004008826 | | 1/2004 |
| WO | 2004009156 | | 1/2004 |
| WO | 2004030716 | A2 | 4/2004 |
| WO | 2004030717 | A2 | 4/2004 |
| WO | 2004064616 | A2 | 8/2004 |
| WO | 2004062710 | A3 | 10/2004 |
| WO | 2004105589 | A2 | 12/2004 |
| WO | 2005044339 | | 5/2005 |
| WO | 2004105589 | A3 | 6/2005 |
| WO | 2005061026 | | 7/2005 |
| WO | 2005123230 | | 12/2005 |
| WO | 2005123230 | A2 | 12/2005 |
| WO | 2006023589 | | 3/2006 |
| WO | 2006124431 | A2 | 11/2006 |
| WO | 2007010164 | A2 | 1/2007 |
| WO | 2007089855 | A2 | 8/2007 |
| WO | 2007146162 | A2 | 12/2007 |
| WO | 2007146162 | A3 | 12/2007 |
| WO | 2008037410 | | 4/2008 |
| WO | 2008051994 | | 5/2008 |
| WO | 2009026603 | | 12/2008 |
| WO | 2009024566 | | 2/2009 |
| WO | 2009026603 | A1 | 3/2009 |
| WO | 2009061608 | | 5/2009 |
| WO | 2009064984 | | 5/2009 |
| WO | 2009067071 | A1 | 5/2009 |
| WO | 2009071103 | | 6/2009 |
| WO | 2009094184 | | 7/2009 |
| WO | 2009132839 | A1 | 11/2009 |
| WO | 2009157877 | A1 | 12/2009 |
| WO | 2009157878 | A1 | 12/2009 |
| WO | 20090157877 | | 12/2009 |
| WO | 2010028860 | | 3/2010 |
| WO | 2010028860 | A1 | 3/2010 |
| WO | 2010042666 | | 4/2010 |
| WO | 2010042666 | A2 | 4/2010 |
| WO | 2010052705 | A1 | 5/2010 |
| WO | 2010062698 | | 6/2010 |
| WO | 2010096659 | | 10/2010 |
| WO | 2010121820 | | 10/2010 |
| WO | 2010102190 | A4 | 11/2010 |
| WO | 2011017215 | A1 | 2/2011 |
| WO | 2011025705 | A1 | 3/2011 |
| WO | 2011072337 | | 8/2011 |
| WO | 2011113572 | A1 | 9/2011 |
| WO | 2012026978 | | 3/2012 |
| WO | 2012042323 | | 4/2012 |
| WO | 2012050781 | | 4/2012 |
| WO | 2012051996 | | 4/2012 |
| WO | 2012067585 | | 5/2012 |
| WO | 2010042666 | A3 | 6/2012 |
| WO | 2012138604 | A2 | 10/2012 |
| WO | 2012148781 | | 11/2012 |
| WO | 2012148786 | | 11/2012 |
| WO | 2012148789 | | 11/2012 |
| WO | 2012162515 | A2 | 11/2012 |
| WO | 20120277551 | | 11/2012 |
| WO | 2012172398 | | 12/2012 |
| WO | 2013019179 | A1 | 2/2013 |
| WO | 2013019994 | A2 | 2/2013 |

(56) References Cited

FOREIGN PATENT DOCUMENTS

| | | |
|---|---|---|
| WO | 2013025844 | 2/2013 |
| WO | 2013025844 A2 | 2/2013 |
| WO | 2013027214 | 2/2013 |
| WO | 2013028809 A2 | 2/2013 |
| WO | 2013028809 A3 | 2/2013 |
| WO | 2013019994 A3 | 4/2013 |
| WO | 2013025844 A3 | 5/2013 |
| WO | 2013103607 A1 | 7/2013 |
| WO | 2013103906 | 7/2013 |
| WO | 2013110906 | 8/2013 |
| WO | 2013110919 | 8/2013 |
| WO | 2013114063 A1 | 8/2013 |
| WO | 2013121162 A1 | 8/2013 |
| WO | 2013140346 | 9/2013 |
| WO | 2013141896 | 9/2013 |
| WO | 2013188861 A1 | 12/2013 |
| WO | 14066254 | 5/2014 |
| WO | 14066255 | 5/2014 |
| WO | 14077082 | 5/2014 |
| WO | 2014117000 | 7/2014 |
| WO | 2014121158 A1 | 8/2014 |
| WO | 2014121162 | 8/2014 |
| WO | 2014121163 | 8/2014 |
| WO | 2014121167 | 8/2014 |
| WO | 2014121169 | 8/2014 |
| WO | 2015071247 A1 | 5/2015 |

OTHER PUBLICATIONS 2017-530641_OA.
Examination report for Australian Application 2015361083 dated Jul. 20, 2017.
Office Action in Chinese Application No. 201480007132.5 dated Jul. 19, 2017.
EP Search Report for Application No. 16204175.0 dated Mar. 29, 2017.
Office Action for Chinese Application 201510713880.1 dated Apr. 1, 2017.
Office Action in Chinese Application 201510713880.1 dated Apr. 1, 2017.
U.S. Appl. No. 13/424,533.
Understanding Dialysate Bicarbonate—A simple approach to understanding a complex equation by Fresenius Medical Care, 2011.
International Search Report, Application PCT/US2016/043948, dated Feb. 2, 2017.
Written Opinion, Application PCT/2016/043948, dated Feb. 2, 2017.
International Search Report, Application PCT/US2016/043935, dated Feb. 2, 2017.
Written Opinion, Application PCT/US2016/043935, dated Feb. 2, 2017.
International Search Report and Written Opinion in App. No. PCT/US2012/049398 dated Feb. 25, 2013.
Office Action in European App. No. 12819714.2 dated Aug. 5, 2016.
PCT/US2014/014343 Written Opinion dated Jan. 2, 2015.
PCT/US2014/014343 International Preliminary Search Report dated Mar. 18, 2015.
European Search Report for EP Appl. No. 1474679.4 dated Aug. 19, 2016.
Office Action for Chinese Application 201510761050.6 dated Aug. 2, 2017.
PCT/US2014/014355 International Search Report and Written Opinion dated May 1, 2014.
PCT/US2014/014355 International Preliminary Report dated Apr. 13, 2015.
EP 14746817.7 European Search Report dated Sep. 27, 2016.
Office Action in Chinese Application No. 201480007132.5 dated Feb. 27, 2017.
Office Action in Chinese Application No. 201280047921.2 dated Jun. 11, 2015.
International Preliminary Report from International Application No. PCT/US2014/014348 dated Jan. 9, 2015.
European Search Report from European Application No. EP 14746193.3 dated Oct. 19, 2016.
European Search Report from European Application No. EP 14746193.3 dated Jun. 8, 2016.
PCT/US2014/014346 Writtent Opinion dated Apr. 10, 2015.
PCT/US2014/014346 International Search Report and Writtent Opinion dated May 23, 2014.
EP 14746415.0 European Search Report dated Aug. 22, 2016.
Office Action in European Application No. EP 14746415.0 dated Apr. 19, 2017.
PCT/US2014/014357 International Search Report and Written Opinion dated May 19, 2014.
PCT/US2014/014357 Written Opinion dated Feb. 18, 2015.
European Search Report in European Application No. EP 14746010.9 dated Sep. 15, 2016.
Office Action in European Application No. 14746415.0 dated Apr. 19, 2017.
U.S. Appl. No. 13/424,490.
U.S. Appl. No. 13/424,517.
Written Opinion for PCT/US2015/060090 dated Feb. 16, 2016.
EP 13733819 Supplementary European Search Report dated Jan. 28, 2015.
EP Search Report and Opinion for Application No. 15193720.8 dated May 2, 2016.
Office action for European Application No. 15193720.8 dated Apr. 25, 2017.
PCT/US2012/051011, International Search Report and Written Opinion, dated Mar. 4, 2013.
Office Action for European Application No. 14746611.4 dated Jan. 3, 2017.
Supplemental Search Report and Search Opinion for European Application No. 14746611.4 dated Aug. 18, 2016.
Examination Report in Australian Application No. AU2014212135 dated May 25, 2017.
Office Action in Chinese Application No. 201480007138.2 dated May 31, 2017.
Office Action in European Application No. 14746193.3 dated Apr. 19, 2017.
European Office Action in Application No. 14746793.0 dated Apr. 13, 2017.
Examination report in Australian Application No. 2014212141 dated May 26, 2017.
European Search Report and Search Opinion for European Application EP15193720 dated May 2, 2016.
Office Action in European Application No. 15193720.8 dated Apr. 25, 2017.
International Preliminary Report on Patentability for PCT2015/060090 dated Jun. 13, 2017.
European Search Report for European Application EP 15193830.5 dated May 4, 2016.
Office Action for European Application No. 15193645.7 dated Apr. 21, 2017.
U.S. Appl. No. 61/480,539, filed Apr. 29, 2011.
U.S. Appl. No. 61/480,535, filed Apr. 29, 2011.
Nedelkov, et. al., Design of buffer exchange surfaces and sensor chips for biosensor chip mass spectrometry, Proteomics, 2002, 441-446, 2(4).
PCT/US2017/025868 International Search Report dated Jun. 29, 2017.
PCT/US2017/025868 Written Opinion dated Jun. 29, 2017.
PCTUS2017025858 International Search Report dated Jun. 29, 2017.
PCTUS2017025858 Written Opinion dated Jun. 29, 2017.
PCTUS2017025876 International Search Report dated Jun. 29, 2017.
PCTUS2017025876 Written Opinion dated Jun. 29, 2017.
Brynda, et. al., The detection of toman 2-microglcbuiin by grating coupler immunosensor with three dimensional antibody networks. Biosensors & Bioelectronics, 1999, 363-368, 14(4).

(56) References Cited

OTHER PUBLICATIONS

Wheaton, et al., Dowex Ion Exchange Resins-Fundamentals of Ion Exchange; Jun. 2000, pp. 1-9. http://www.dow.com/scripts/litorder.asp?filepath=liquidseps/pdfs/noreg/177-01837.pdf.
Zhong, et. al., Miniature urea sensor based on H(+)-ion sensitive field effect transistor and its application in clinical analysis, Chin. J. Biotechnol., 1992, 57-65. 8(1).
PCT/US2012/034331, International Search Report and Written Opinion dated Jul. 9, 2012.
Roberts M, The regenerative dialysis (REDY) sorbent system. Nephrology, 1998, 275-278:4.
U.S. Appl. No. 61/480,544.
U.S. Appl. No. 61/480,541, filed Apr. 29, 2011.
Hemametrics, Crit-Line Hematocrit Accuracy, 2003, 1-5, vol. 1, Tech Note No. 11 (Rev. D).
Weissman, S., et al., Hydroxyurea-induced hepatitis in human immunodeficiency virus-positive patients. Clin. Infec. Dis, (Jul. 29, 1999): 223-224.
PCT/US2012/034334, International Search Report, dated Jul. 6, 2012.
PCT/US2012/034335, International Search Report, dated Sep. 5, 2012.
PCT/US/2012/034327, International Search Report, dated Aug. 13, 2013.
PCT/US/2012/034329, International Search Report, dated Dec. 3, 2012.
EP13182115.9-1651 European Search Report, dated Feb. 3, 2014.
International Search Report from PCT/US2012/051946 dated Mar. 4, 2013.
U.S. Appl. No. 61/526,209.
Written Opinion of the International Searching Authority for PCT/US2012/049398 dated Feb. 25, 2013.
Wang, Fundamentals of intrathoracic impedance monitoring in heart failure, Am. J. Cardiology, 2007, 3G-10G: Suppl.
PCT/US2014/067650 International Search Report Written Opinion dated Mar. 9, 2015.
Bleyer, et al, Kidney International. Jun. 2006; 69(12):2268-2273.
U.S. Appl. No. 29/446,285, filed Feb. 1, 2013.
Marchant, et. al., In vivo Biocompatibility Studies 1: The Cage Implant System and a Biodegradable Hydrogel, J. Biomed. Mat. Res., 1983, 301-325: 17.
Bleyer, et. al., Sudden and cardiac death rated in hemodialysis patients, Kidney International. 1999, 1553-1559: 55.
PCT/US2012/025711, International Search Report dated Jul. 4, 2012.
PCT/US2013/020404, International Search Report, dated Jan. 4, 2013.
PCT/US2012/034333, International Preliminary Report on Patentability, dated Oct. 29, 2013.
PCT/US2012/034333, International Search Report, dated Aug. 29, 2012.
PCT/US2012/034333, International Search Report, dated Aug. 29, 2013.
PCT/US2012/051011, International Search Report, dated Jan. 17, 2014.
PCT/US2012/034330, International Preliminary Report on Patentability, dated Oct. 29, 2013.
Culleton, BF et al. Effect of Frequent Nocturnal Hemodialysis vs. Conventional Hemodialysis on Left Ventricular Mass and Quality of Life. 2007 Journal of the American Medical Association 298 (11), 1291-1299.
U.S. Appl. No. 13/757,722, filed Feb. 1, 2013.
U.S. Appl. No. 13/757,794, filed Feb. 2, 2012.
U.S. Appl. No. 13/791,755, filed Mar. 8, 2013.
U.S. Appl. No. 13/424,479, filed Nov. 1, 2012.
U.S. Appl. No. 13/757,792, filed Feb. 2, 2013.
U.S. Appl. No. 13/757,794, filed Feb. 2, 2013.
U.S. Appl. No. 13/837,287, filed Mar. 15, 2013.
U.S. Appl. No. 13/424,429, filed Nov. 1, 2012.
Redfield, et. al, Restoration of renal response to atrial natriuretic factor in experimental low-output heat failure, Am. J. Physiol., Oct. 1, 1989, R917-923:257.
Rogoza, et. al., Validation of A&D UA-767 device for the self-measurement of blood pressure, Blood Pressure Monitoring, 2000, 227-231, 5(4).
Lima, et. al., An electrochemical sensor based on nanostructure hollsndite-type manganese oxide for detection of potassium ion, Sensors, Aug. 24, 2009, 6613-8625, 9.
Maclean, et, al., Effects of hindlimb contraction on pressor and muscle interstitial metabolite responses in the cat, J. App. Physiol., 1998, 1583-1592, 85(4).
U.S. Appl. No. 13/757,693, filed Feb. 1, 2013.
PCT Application, PCT/US20013/020404, filed Jan. 4, 2013.
U.S. Appl. No. 13/424,525.
U.S. Appl. No. 13/836,973, filed Mar. 15, 2013.
U.S. Appl. No. 14/259,655, filed Apr. 23, 2014.
U.S. Appl. No. 14/259,589, filed Apr. 23, 2014.
U.S. Appl. No. 13/757,693, filed Jan. 4, 2013.
U.S. Appl. No. 13/836,079, filed Mar. 15, 2013.
U.S. Appl. No. 14/240,129, filed Aug. 22, 2013.
PCT/US2014/014346 International Search Report and Written Opinion.
U.S. Appl. No. 13/835,735, filed Mar. 15, 2013.
PCT/US2014/014345 International Search Report and Written Opinion, dated May 2014.
U.S. Appl. No. 13/835,735 IDS, filed Jun. 13, 2013.
Ronco et al. 2008, Cardiorenal Syndrome, Journal American College Cardiology, 52:1527-1539, Abstract.
Overgaard, et. al., Activity-induced recovery of excitability in K+-depressed rat soleus muscle, Am. J. P 280: R48-R55, Jan. 1, 2001.
Overgaard. et. al., Relations between excitability and contractility in rate soleusmuscle: role of the Na+-K+ pump and Na+-K-S gradients. Journal of Physiology, 1999, 215-225, 518(1).
Coast, et al. 1990, An approach to Cardiac Arrhythmia analysis Using Hidden Markov Models, IEEE Transactions on Biomedical Engineering. 1990, 37(9):826-835.
Weiner, et. al., Article: Cardiac Function and Cardiovascular Disease in Chronic Kidney Disease, Book: Primer on Kidney Diseases (Author: Greenberg, et al), 2009,499-505, 5th Ed., Saunders Elsevier, Philadelphia, PA.
U.S. Appl. No. 61/480,532.
U.S. Appl. No. 13/424,479.
U.S. Appl. No. 61/480,530.
U.S. Appl. No. 61/480,528, filed Apr. 29, 2011.
Secemsky, et. al, High prevalence of cardiac autonomic dysfunction and T-wave alternans in dialysis patients. Heart Rhythm, Apr. 2011, 592-598 : vol. 8, No. 4.
Wei, et. al., Fullerene-cryptand coated piezoelectric crystal urea sensor based on urease, Analytica Chimica Acta, 2001,77-85:437.
Gambro AK 96 Dialysis Machine Operators Manual, Dec. 2012. p. 1-140.
Gambro AK 96 Dialysis Machine Operators Manual, Dec. 2012. p. 141-280.
Gambro AK 96 Dialysis Machine Operators Manual, Dec. 2012. p. 281-420.
Gambro AK 96 Dialysis Machine Operators Manual, Dec. 2012. p. 421-534.
European Search Report 12819714.2-1651/2739325 PCT/US2012049398, dated Jun. 12, 2015.
PCT/US2014/14343 Intl Search Report & Written Opinion, dated May 9, 2014.
PCT/US2014/014350 International Search Report and Written Opinion dated May 2014.
U.S. Appl. No. 13/368,225, filed Feb. 7, 2012.
EP 14746793 Supplementary European Search Report dated Aug. 18, 2016.
EP 14746791 Supplementary European Search Report dated Aug. 19, 2016.
EP 14746799 Supplementary European Seach Report dated Aug. 18, 2016.

(56) References Cited

OTHER PUBLICATIONS

Leifer et al., A Study on the Temperature Variation of Rise Velocity for Large Clean Bubbles, J. Atmospheric & Oceanic Tech., vol. 17, pp. 1392-1402, Oct. 2000.
Talaia, Terminal Velocity of a Bubble Rise in a Liquid Column, World Acad. of Sci., Engineering & Tech., vol. 28, pp. 264-268, Published Jan. 1, 2007.
The FHN Trial Group. In-Center. Hemodialysis Six Times per Week versus Three Times per Week, New England Journal of Medicine, 2010 Abstract.
PCT/US2012/034332, International Search Report, dated Jul. 5, 2012.
Office Action in U.S. Appl. No. 13/757,717 dated Dec. 26, 2014.
Office Action in U.S. Appl. No. 13/757,709 dated Jun. 6, 2015.
Office Action in U.S. Appl. No. 13/757,709 dated Jan. 7, 2016.
Office Action in U.S. Appl. No. 13/757,728 dated Jan. 8, 2016.
Office Action in U.S. Appl. No. 13/757,728 dated Aug. 12, 2016.
Office Action in U.S. Appl. No. 13/757,796 dated Apr. 13, 2015.
Office Action in U.S. Appl. No. 13/757,796 dated Dec. 21, 2015.
Office Action in U.S. Appl. No. 13/836,538 dated Aug. 19, 2015.
Siegenthaler, et al., Pulmonary fluid status monitoring with intrathoracic impedance, Journal of Clinical Monitoring and Computing, 24:449-451, published Jan. 12, 2011.
Office Action in U.S. Appl. No. 13/836,538 dated Jan. 11, 2016.
Office Action in U.S. Appl. No. 13/836,538 dated Apr. 27, 2016.
Office Action in U.S. Appl. No. 13/757,722 dated May 19, 2016.
Office Action in U.S. Appl. No. 13/757,693 dated Nov. 13, 2015.
Office Action in U.S. Appl. No. 13/757,693 dated May 23, 2016.
Office Action in U.S. Appl. No. 13/757,794 dated Oct. 21, 2015.
Office Action in U.S. Appl. No. 13/757,794 dated May 2, 2016.
Office Action in U.S. Appl. No. 13/424,525 dated Aug. 11, 2015.
Office Action in U.S. Appl. No. 13/424,525 dated Feb. 25, 2016.
Office Action in U.S. Appl. No. 13/424,525 dated Jun. 17, 2016.
Office Action in U.S. Appl. No. 13/424,525 dated Oct. 20, 2016.
Office Action in U.S. Appl. No. 13/424,479 dated Nov. 24, 2014.
Office Action in U.S. Appl. No. 14/566,686 dated Apr. 28, 2016.
Office Action in U.S. Appl. No. 13/424,533 dated Oct. 22, 2013.
Office Action in U.S. Appl. No. 13/424,533 dated Apr. 18, 2014.
Office Action in U.S. Appl. No. 13/424,533 dated Jan. 5, 2015.
Office Action in U.S. Appl. No. 13/424,533 dated Jun. 2, 2015.
Office Action in U.S. Appl. No. 13/424,533 dated Jul. 14, 2016.
Welgemoed, T.J., Capacitive Deionization Technology: An Alternative to desalination Solution, Desalination 183 (2005) 327-340.
European Search Report for App. No. 15193645.7, dated Apr. 15, 2016.
European Search Report in App. No. 15193720.8 dated Apr. 26, 2016.
EP. App. 14746193.3 Search Report dated Oct. 19, 2016.
Office Action in U.S. Appl. No. 14/555,393 dated May 4, 2016.
Office Action in U.S. Appl. No. 14/555,393 dated Nov. 1, 2016.
Office Action in U.S. Appl. No. 14/555,414 dated May 4, 2016.
Office Action in U.S. Appl. No. 14/555,414 dated Nov. 3, 2016.
Office Action in U.S. Appl. No. 13/586,824 dated Dec. 21, 2015.
Office Action in U.S. Appl. No. 13/586,824 dated Jun. 4, 2016.
Office Action in Chinese Application No. 201480007138.2 dated Sep. 28, 2016.
Ruperez et al., Comparison of a tubular pulsatile pump and a volumetric pump for continuous venovenous renal replacement therapy in a pediatric animal model, 51 Asaio J. 372, 372-375 (2005).
St. Peter et al., Liver and kidney preservation by perfusion, 359 The Lancet 604, 606(2002).
Dasselaar et al., Measurement of relative blood volume changes during hemodialysis: merits and limitations, 20 Nephrol Dial Transpl. 2043, 2043-2044 (2005).
Ralph T. Yang, Adsorbents: Fundamentals and Applications 109 (2003).
Henny H. Billett, Hemoglobin and Hematocrit, in Clinical Methods: The History, Physical, and Laboratory Examinations 719(HK Walker, WD Hall, & JW Hurst ed., 1990).
Office Action in U.S. Appl. No. 13/565,733 dated Jan. 11, 2016.
Office Action in U.S. Appl. No. 13/565,733 dated Jun. 11, 2015.
U.S. Appl. No. 13/424,454.
Office Action in U.S. Appl. No. 13/586,824 dated Jun. 4, 2015.
Office Action in U.S. Appl. No. 13/757,792 dated Jun. 2, 2016.
Office Action in U.S. Appl. No. 13/835,735 dated Oct. 13, 2015.
Office Action in U.S. Appl. No. 13/836,079 dated Apr. 17, 2015.
Office Action in U.S. Appl. No. 13/836,079 dated Jun. 30, 2016.
Office Action in U.S. Appl. No. 13/791,755 dated Mar. 16, 2016.
Office Action in U.S. Appl. No. 13/791,755 dated Aug. 9, 2016.
Office Action in U.S. Appl. No. 13/835,735 dated Jun. 16, 2016.
Office Action in U.S. Appl. No. 13/836,079 dated Nov. 6, 2015.
Office Action in U.S. Appl. No. 13/791,755 dated Sep. 10, 2015.
Office Action in U.S. Appl. No. 13/791,755 dated Apr. 20, 2015.
U.S. Appl. No. 13/424,467.
Office Action in U.S. Appl. No. 14/259,589 dated Nov. 4, 2016.
Office Action in U.S. Appl. No. 14/261,651 dated Aug. 25, 2016.
International Search Report from International Application No. PCT/US2014/014347 dated May 9, 2014.
International Search Report for PCT/US2015/060090 date of completion is Feb. 9, 2016 (3 pages).
St. Peter et al., Liver and Kidney Preservation by perfusion, 369 The Lancet 604, 606 (2002).
Office Action for Chinese Application 20148007136.3, dated Jun. 2, 2016.
Office Action in Chinese Application No. 20148007136.3 dated Jun. 15, 2017.
Office Action for Chinese Application 20148007136.3, dated Jan. 26, 2017.
Franks, Gene, Cabon Filtration: What it does, What it doesnt, Mar. 14, 2012, pp. 1-3.
Franks, Gene, Carbon Filtration: What it does, What it doesnt, Mar. 14, 2012, pp. 1-3.
PCT/US2014/014352 International Search Report and Written Opinion dated Jul. 7, 2014.
PCT/US2014/014352 International Prelminary Report on Patentability, dated Aug. 14, 2015.
Hamm et al,. Sorbent regenerative hemodialysis as a potential cuase of acute hypercapnia, Kidney International, vol. 21, (1982), pp. 416-418.
Office Action in Chinese App. No. 201580067284.9, dated Oct. 8, 2019.
Chinese Office Action for App. No. 201580067284.9, dated Mar. 6, 2020.
Office Action in European App. No. 19154609.2, dated Mar. 10, 2020.
Brazilian Search Report for App. No. BR112017012326-6, dated Mar. 13, 2020.
Office Action in Chinese Application No. 201580067284.9, dated Mar. 6, 2020.
Office Action in European App. No. 19219498.3, dated Mar. 26, 2020.

\* cited by examiner

DEGASSING SYSTEM FOR DIALYSIS

CROSS-REFERENCE TO RELATED APPLICATIONS

This application is a Continuation-in-part of U.S. patent application Ser. No. 14/566,686 filed Dec. 10, 2014, now U.S. Pat. No. 9,713,665.

This application also claims benefit of and priority to U.S. patent application Ser. No. 15/618,187 filed Jun. 9, 2017, which is a Continuation of U.S. patent application Ser. No. 14/566,686 filed Dec. 10, 2014, now U.S. Pat. No. 9,713,665, and the disclosures of each of the above-identified applications are hereby incorporated by reference in their entirety.

FIELD OF THE INVENTION

The invention relates to a degassing vessel and related systems and methods that can remove certain gases such as carbon dioxide from a dialysis system with minimal foaming inside the degassing vessel. The invention further relates to mechanical systems and methods for degassing a dialysate or any fluid used for, during or resulting from dialysis.

BACKGROUND

In dialysis systems including sorbent based systems, gas such as carbon dioxide can be created as part of sorbent dialysis. In particular, carbon dioxide can be generated as the gas is formed during urea breakdown as spent dialysate flows through a sorbent cartridge. The bicarbonate buffer system can also contribute to the creation of excess carbon dioxide in dialysate. Further, dialysate can contain dissolved oxygen and nitrogen gas that crosses the dialysis membrane from the patient's blood. Dissolved gases such as nitrogen and oxygen can also be present in water that is used to initially prepare a dialysate. The resulting gases from any one of the sources can go into solution in dialysate and form gas bubbles.

Removal of carbon dioxide and other dissolved and undissolved gases can be important for maintaining a required pH or maintaining certain fluid conditions such as a bicarbonate or ion concentration. For example, a desired partial pressure of carbon dioxide may be required for safe operation during dialysis. Further, excesses gases can be removed to avoid creating gas bubbles. Gas bubbles can interfere with the smooth pumping of dialysate in a dialysate loop and can interfere with sensors in the dialysate flow path and reduce diffusive clearance across the dialysis membrane. Gas bubbles can also result in a dangerous condition if gas crosses the dialyzer membrane into an extracorporeal circuit and creates gas bubbles in blood returning to a patient. Known systems suffer from excess foaming within the degassing vessel, which can reduce accuracy in measuring fluid levels and impede fluid flow through the degassing system.

The degassers known in the art oftentimes fail to efficiently remove dissolved gases, such as carbon dioxide, from fluid, or do not provide control over the amount of carbon dioxide removed. Hence, there is a need for a degasser that can remove large amounts of dissolved carbon dioxide from solution, while providing control over the amount of dissolved and undissolved gases removed from fluid before, during and after dialysis therapy. There is also a need for a degasser having the small size and weight necessary for a portable device. There is a further need for a degassing system that can reduce foaming within the degassing vessel.

SUMMARY OF THE INVENTION

The first aspect of the invention is drawn to a degassing vessel. In any embodiment, the degassing vessel can comprise a fluid inlet in the degassing vessel fluidly connectable to a dialysate flow path; a liquid outlet in the degassing vessel fluidly connectable to the dialysate flow path; a gas outlet fluidly connectable to a vacuum pump; and a degas sprayer fluidly connected to the fluid inlet.

In any embodiment, the degas sprayer can direct liquid downwardly into the degassing vessel.

In any embodiment, the degassing vessel can comprise a spray chamber and a float chamber; the spray chamber fluidly connected to the float chamber; wherein the degas sprayer is positioned above the spray chamber.

In any embodiment, the spray chamber can have a substantially conical shape.

In any embodiment, the liquid outlet can be positioned in a bottom portion of the spray chamber.

In any embodiment, the gas outlet can be positioned between the spray chamber and the float chamber.

In any embodiment, the degassing vessel can comprise a level sensor in the float chamber.

In any embodiment, the level sensor can comprise one or more of: a float with a magnet and a linear array of Hall effect sensors, an ultrasonic sensor, and a capacitive sensor.

In any embodiment, the degassing vessel can comprise a temperature sensor in the liquid outlet.

In any embodiment, the degassing vessel can comprise a pressure sensor in the gas outlet.

In any embodiment, the degassing vessel can comprise a valve positioned between the gas outlet and the vacuum pump.

In any embodiment, the degassing vessel can comprise a vent valve positioned between a vent and the gas outlet.

Any of the features disclosed as being part of the first aspect of the invention can be included in the first aspect of the invention, either alone or in combination.

The second aspect of the invention is drawn to a system. In any embodiment, the system can comprise a dialysate flow path comprising a degassing flow loop; the degassing flow loop comprising a degassing vessel having a fluid inlet fluidly connected to a degas sprayer at a top portion of the degassing vessel, a liquid outlet at a bottom portion of the degassing vessel, and a gas outlet at a top portion of the degassing vessel; a vacuum pump fluidly connected to the gas outlet; a first fluid line fluidly connecting the liquid outlet to a second fluid line fluidly connected to the fluid inlet, the first fluid line comprising a fluid pump; a third fluid line fluidly connecting the second fluid line to the dialysate flow path; and a controller controlling the vacuum pump and the fluid pump.

In any embodiment, the degassing flow loop can be parallel to the dialysate flow path; and a flow rate of the degassing flow loop can be controlled independently of a flow rate of the dialysate flow path.

In any embodiment, the system can comprise a first pressure sensor in the degassing flow loop upstream of the fluid inlet and a second pressure sensor in the degassing flow loop in the gas outlet.

In any embodiment, the controller can control a first valve positioned between the vacuum pump and the gas outlet and/or a vent valve positioned between a vent and the gas outlet based on an absolute pressure in a headspace of the degassing vessel.

In any embodiment, the controller can control the first valve and/or the vent valve to maintain a carbon dioxide level in the third fluid line of between 40 mmHg and 150 mmHg pCO2.

In any embodiment, the system can comprise at least one valve positioned in the third fluid line between the gas outlet and a vent.

In any embodiment, the system can comprise an ambient pressure sensor.

In any embodiment, the degassing vessel can comprise a level sensor in communication with the controller; the level sensor comprising one or more of: a float with a magnet and a linear array of Hall effect sensors, an ultrasonic sensor, and a capacitive sensor.

Any of the features disclosed as being part of the second aspect of the invention can be included in the second aspect of the invention, either alone or in combination.

DETAILED DESCRIPTION OF THE INVENTION

Figure 1A:
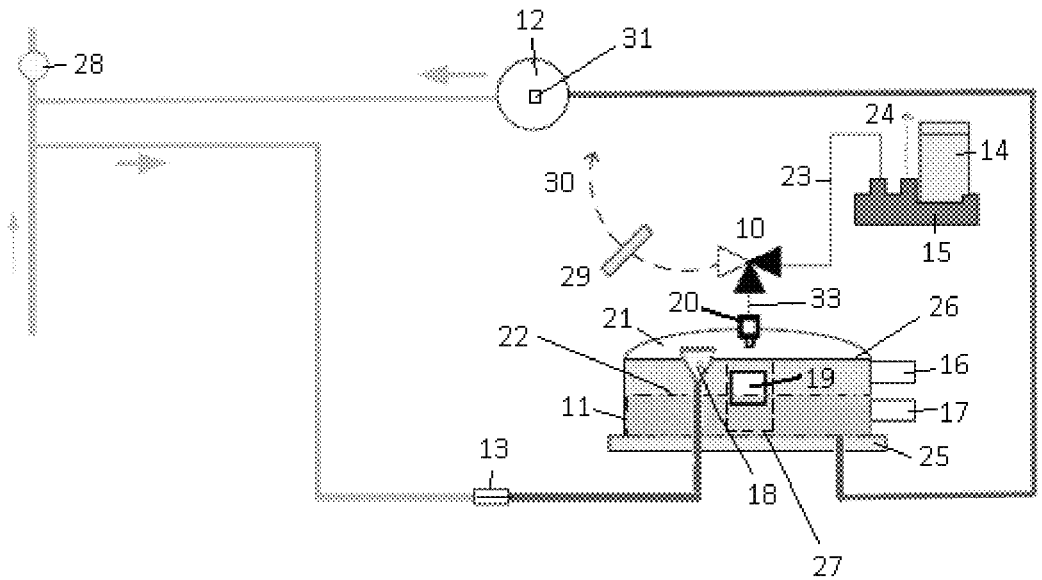
FIG. 1A shows a schematic of a degassing module for use in sorbent dialysis configured to degas dialysate.

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. By way of example, "an element" means one element or more than one element.

The term "absolute pressure" refers to a pressure of a liquid, gas, or combination thereof, relative to a vacuum.

An "ambient pressure sensor" is a pressure sensor positioned to measure a pressure outside of a container, system, or fluid line, such as atmospheric pressure.

The term "bottom portion" refers to a portion of a component at a height lower than the center of the component when positioned for normal use.

A "capacitive sensor" is a sensor that measures distance to a conductive object by measuring changes in capacitance as the conductive object closer to or further away from the sensor.

The term "carbon dioxide sensor" refers to devices that can detect or measure the concentration of carbon dioxide in a fluid, gas, or combination thereof.

The terms "communicate" and "communication" include, but are not limited to, the connection of system electrical elements, either directly or remotely, for data transmission among and between said elements. The terms also include, but are not limited to, the connection of system fluid elements enabling fluid interface among and between said elements.

The term "comprising" includes, but is not limited to, whatever follows the word "comprising." Thus, use of the term indicates that the listed elements are required or mandatory but that other elements are optional and may or may not be present.

A "conical shape" or "substantially conical shape" refers to a three-dimensional shape of a component that has a larger diameter on a first side than on a second side and inwardly or outwardly tapering walls connecting the first side and second side.

The term "consisting of" includes and is limited to whatever follows the phrase "consisting of." Thus, the phrase indicates that the limited elements are required or mandatory and that no other elements may be present. The term "consisting essentially of" includes whatever follows the term "consisting essentially of" and additional elements, structures, acts or features that do not affect the basic operation of the apparatus, structure or method described.

The terms "control," "controlling," or "controls" can refer to the ability of one component to direct the actions of a second component.

The term "controlled independently" refers to the ability to vary one parameter of a system without varying a second parameter of the system.

A "controller," "controller," "processor," or "microprocessor" is a device which monitors and affects the operational conditions of a given system. The operational conditions are typically referred to as output variables of the system wherein the output variables can be affected by adjusting certain input variables.

A "degas sprayer" is a component that atomizes or increases the surface area to volume ratio of a fluid.

A "degasser" is a component that is capable of removing dissolved and undissolved gasses from fluids. The term "degasser" can encompass a degassing vessel, and a fluid pump and a vacuum pump connected to the degassing vessel and working in concert to create a vacuum in the fluid flowing through the degassing vessel and to evacuate gas from the degassing vessel.

A "degassing flow loop" is a portion of a fluid pathway that conveys a dialysate from a dialysate flow loop to a degasser and back to the dialysate flow loop.

A "degassing vessel" or a "degas vessel" is a component of a degasser, and can be any structure having an inlet through which fluid enters the vessel, a first outlet through which gas removed from the fluid may pass, and a second outlet through which fluid can exit the vessel.

The term "dialysate flow loop," "dialysate flow path" or "dialysate conduit flow path" refers to any portion of a fluid pathway that conveys a dialysate and is configured to form at least part of a fluid circuit for hemodialysis, hemofiltration, ultrafiltration, hemodiafiltration or ultrafiltration. Optionally, the fluid pathway can contain priming fluid during a priming step or cleaning fluid during a cleaning step.

"Dialysis" is a type of filtration, or a process of selective diffusion through a membrane. Dialysis removes solutes of a specific range of molecular weights via diffusion through a membrane from a fluid to be dialyzed into a dialysate. During dialysis, a fluid to be dialyzed is passed over a filter membrane, while dialysate is passed over the other side of that membrane. Dissolved solutes are transported across the filter membrane by diffusion between the fluids. The dialysate is used to remove solutes from the fluid to be dialyzed. The dialysate can also provide enrichment to the other fluid.

The term "downstream" refers to a position of a first component in a flow path relative to a second component wherein fluid, gas, or combinations thereof, will pass by the second component prior to the first component during normal operation. The first component can be said to be "downstream" of the second component, while the second component is "upstream" of the first component.

The terms "downward" or "downwardly" refer to a direction from a higher elevation to a lower elevation when the system is configured for normal use.

A "float" is a component with a density lower than that of a fluid, causing the float to raise to the top of the fluid.

A "float chamber" is a chamber or other portion of a component that contains a fluid level sensor. In certain embodiments, the fluid level sensor can operate using a float located within the float chamber.

"Flow rate" refers to a volume of a fluid, gas, or combination thereof, moved per unit time.

The term "fluidly connectable" refers to the ability to provide passage of fluid, gas, or combinations thereof, from one point to another point. The ability to provide such passage can be any mechanical connection, fastening, or forming between two points to permit the flow of fluid, gas, or combinations thereof. The two points can be within or between any one or more of compartments, modules, systems, components, and rechargers, all of any type.

The term "fluidly connected" refers to a particular state or configuration of one or more components such that fluid, gas, or combination thereof, can flow from one point to another point. The connection state can also include an optional unconnected state or configuration, such that the two points are disconnected from each other to discontinue flow. It will be further understood that the two "fluidly connectable" points, as defined above, can from a "fluidly connected" state. The two points can be within or between any one or more of compartments, modules, systems, components, and rechargers, all of any type.

The term "fluid inlet" refers to a conduit or opening through which fluid, gas, or a combination thereof, can enter a component or apparatus.

A "fluid line" can refer to a tubing or conduit through which a fluid, gas, or a combination thereof can pass. The fluid line can also contain air during different modes of operation such as cleaning or purging of a line.

A "fluid pump" is a pump used to move fluid, gas, or a combination thereof, throughout a system.

The term "gas outlet" refers to a conduit or opening through which gas can exit a component or apparatus. In certain embodiments, a gas outlet can also allow fluids to enter or exit the component.

The term "headspace" refers to a portion of a container or vessel containing air that is above a liquid.

A "level sensor" is a component capable of determining the level of a fluid in a container. The terms "upper level sensor" and "lower level sensor" refer to the respective positions of level sensors.

A "linear array of Hall effect sensors" is a set of components that measure a magnetic field in order to measure a distance to a magnet. In certain embodiments, the linear array can include multiple Hall sensors in a vertical line, each sensor measuring a distance to the magnetic object in order to calculate the position of the magnetic object.

The term "liquid outlet" refers to a conduit or opening through which liquid can exit a component or apparatus. In certain embodiments, a gas can exit the component through the liquid outlet during cleaning, disinfection, or set up of the component.

A "magnet" is a material capable of creating a magnetic field around itself.

The term "maintain a carbon dioxide level" refers to controlling a system to prevent the concentration of carbon dioxide in a fluid from substantially deviating from a predetermined value or range.

The term "parallel," as used to describe two or more flow paths, refers to a configuration wherein fluid, gas, or a combination thereof can only travel through one of the two or more flow paths without being recirculated.

The terms "pressure meter" and "pressure sensor" refer to a device for measuring the pressure of a gas, a fluid, or a combination thereof in a vessel, container, or fluid line.

A "spray chamber" is a chamber or other portion of a component into which a fluid can be sprayed.

The term "temperature sensor" refers to a device for measuring the temperature of a fluid, a gas, or a combination thereof in a vessel, container, or fluid line.

The term "top portion" refers to the portion of a component at a height higher than the center of a component when positioned for normal use.

An "ultrasonic sensor" is a sensor that measures distance to an object by determining a length of time necessary for an ultrasonic wave to reach the object and reflect back to the sensor.

The term "upstream" refers to a position of a first component in a flow path relative to a second component, wherein fluid, gas, or a combination thereof, will pass by the first component prior to the second component during normal operation. The first component can be said to be "upstream" of the second component, while the second component is "downstream" of the first component.

A "vacuum pump" is a pump used to create negative pressure in a component.

A "valve" is a device capable of directing the flow of fluid, gas, or a combination thereof, by opening, closing or obstructing one or more pathways to allow the fluid, gas, or combination thereof to travel in a particular path. One or more valves configured to accomplish a desired flow can be configured into a "valve assembly."

A "vent valve" is a valve that controls the movement of a gas into and out of a vent. In certain embodiments, a vent valve can also allow fluids to enter or exit the vent.

The term "vent" as referred to in relationship to a gas, refers to a means for permitting the escape of a gas from a defined portion of a system, vessel, container, or fluid line. In certain embodiments, fluids may also escape through the vent.

Degassing Vessel

The first, second and third aspects of the invention relate to a degasser and related systems and methods for removing gas, and specifically carbon dioxide, generated from the breakdown of urea in the sorbent cartridge. A degassing module in accordance with the first, second and third aspects of the invention is shown in FIG. 1A. The direction of dialysate flow is shown by the arrows. The degassing module can be placed in the dialysis circuit preferably at a point between the sorbent cartridge (not shown) and the dialyzer (not shown). The degassing module can have a degassing flow loop providing fluid flow that is in parallel to the dialysate flow path. The parallel configuration allows the fluid flow through the degassing loop to be independent of the fluid flow rate through the dialyzer such that the fluid flow rate through the degassing loop can be either less than or greater than the dialysate flow rate through the dialyzer. Thus, the parallel configuration provides control flexibility to adjust the degassing loop flow rate for optimal degassing without requiring the dialysate flow rate through the dialyzer to change. Alternatively, the fluid flow through the degassing module can be arranged in series with the dialysate flow to the dialyzer.

As the dialysate enters the degassing module, the dialysate can pass a degas restrictor 13 of FIG. 1A. The degas restrictor 13 can serve to restrict the flow of fluid through the degassing system. The degas restrictor 13 may be a narrow tube or any portion of the flow path that can be narrowed in a controlled fashion. For example, restriction can be provided by a portion of the flow path being crushable and having roller portions to create a portion of the flow path having a narrowed inner diameter to thereby restrict flow. Any other mechanical structures known to those of ordinary skill to restrict flow is also contemplated by the first, second and third aspects of the invention. The fluid pump 12, fluidly connected to the degas restrictor 13, can pull fluid through the degas restrictor 13, creating a reduced pressure in the degassing vessel 11 side of the degas restrictor 13. The fluid pump 12 provides energy necessary to remove the degassed liquid from the low pressure of the degassing vessel 11 and return the degassed liquid to the higher pressure of the main dialysate flow path. A vacuum can be created in the degassing vessel 11 side of the degas restrictor 13. A pressure sensor (not shown) can be placed after the degas restrictor 13 to determine the pressure of fluid in the degasser. Importantly, the fluid pump 12 of the present invention can be located downstream of the degassing vessel 11 to allow for improved removal of carbon dioxide. The vacuum that can be created by pulling the fluid through the degas restrictor 13 helps to draw dissolved gases, including carbon dioxide, out of solution by reducing the pressure of the fluid below the partial pressure of the dissolved gas in the liquid. The degas restrictor 13 need not be a separate component. Instead, the fluid inlet of the degassing vessel 11 can be narrow, and therefore operate as a flow restrictor. Vacuum pump 14 on the gas removal pump assembly 15 can be fluidly connected to the degassing vessel 11 by gas removal line 23 and can desirably remove the gases in the low pressure environment inside degassing vessel 11 via mechanical vent valve 20. The fluid enters the degassing vessel 11, by crossing through the base 25 of the degassing vessel 11 and through degas sprayer 18. However, there is no particular requirement of the first, second or third aspects of the invention for the fluid to enter or exit through the base. The degas sprayer 18 creates a thin spray or mist, which can increase release of dissolved gases from solution by increasing the surface area of liquid in contact with the low pressure atmosphere in the gas space 21 inside degassing vessel 11 to increase the rate at which gas can be liberated from the liquid. In certain embodiments, the fluid can enter the degassing vessel 11 at other locations than the base 25. For example, fluid can enter the degassing vessel 11 at a location on the side of the degassing vessel 11. The degas sprayer 18 can be positioned within the degassing vessel 11 so that the degas sprayer 18 is above the maximum fluid level 26. The degas sprayer 18 is optional and not required to remove carbon dioxide or other gases from the dialysate solution. Flow restrictions in degas sprayer 18 cause sufficient pressure reduction in the fluid and degas restrictor 13 is not required. Carbon dioxide and other gases collect in the gas space 21 of the degassing vessel 11 and leave the degassing vessel 11 through vent valve 10, positioned on a connector 33 fluidly connected to the degassing vessel 11. Although depicted as a 3-way valve, vent valve 10 can be any combination of one or more valves suitable for accomplishing the desired control of gas flow. In FIG. 1A, the pathways open in vent valve 10 are shown in black. Vacuum pump 14 on the gas removal pump assembly 15 is attached to the degassing vessel 11 by gas removal line 23, and provides the force necessary to move gases from the lower pressure degassing vessel 11 out into the atmosphere. The vacuum pump 14 exerts a vacuum that is greater than or equal to the vacuum created by the fluid pump 12 pulling fluid through the degas restrictor 13, which allows the removal of the accumulated gas from the degassing vessel 11.

The degassing vessel 11 of the first, second and third aspects of the invention can be operated at a pressure lower than atmospheric pressure due to the presence of vacuum pump 14. By maintaining the degassing vessel 11 at a pressure less than atmospheric pressure, carbon dioxide present in the fluid can be more easily removed than in the absence of the described system of pumps of the first, second and third aspects of the invention. The vent valve 10 can allow gas to leave directly into the atmosphere through filter 29, as represented by arrow 30. The filter 29 is a particle filter that serves to remove particulate matter from air flowing through filter 29. The gases may travel through gas removal line 23, to the gas removal pump assembly 15 and into the atmosphere as represented by arrow 24.

Vent valve 10 can be a three way valve, as shown in FIG. 1A. This can allow air to be removed from the degassing vessel 11 through the gas removal line 23, and also allow air to be drawn into the degas flow loop when fluid is being drained from the system. Overflow float 19 and mechanical vent valve 20 can provide a mechanism for an automatic shutdown, preventing fluid from leaving the degassing vessel 11 through the vent valve 10, but allowing air to be added or removed during filling or draining of the system. If the fluid level in the degassing vessel 11 reaches above a certain point, overflow float 19 can block, either directly or indirectly, the fluid from passing through mechanical vent valve 20. The maximum fluid level in the degassing vessel 11 can be shown by line 26, while the minimum fluid level can be shown by line 22. A degas float channel 27 can be used to ensure that the overflow float 19 properly engages with the mechanical vent valve 20. The degas float channel 27 can be placed directly underneath the mechanical vent valve 20 so that when the overflow float 19 rises to the top of the degassing vessel 11, the overflow float 19 will properly cover the mechanical vent valve 20. Alternatively, the float can move an actuator so that the mechanical vent valve 20 is closed. The degas float channel 27 can be made with a fluid permeable substance, such as mesh, so that fluid can still move freely through the degassing vessel 11. In certain embodiments, the function of the degas float channel 27 can be accomplished by a rod through the overflow float 19 wherein the rod is anchored to the degassing vessel 11. The overflow float 19 can be tethered to actuators (not shown). If the overflow float 19 rises, the tethers (not shown) can activate the actuators by pulling on the actuators to either shut off, or modulate the pump rate of, the vacuum pump 14 and fluid pump 12.

Lower level sensor 17 and upper level sensor 16 can sense the fluid level in the degassing vessel 11. The fluid level in the degassing vessel 11 can be a function of the vacuum created by fluid pump 12 and vacuum pump 14 working independently or in concert. The pump rate of the fluid pump 12 and vacuum pump 14 can be adjusted as necessary to maintain the correct fluid level in the degassing vessel 11. The lower level sensor 17 and upper level sensor 16 can be in electronic communication with a controller (not shown). The pump rates of the fluid pump 12 and vacuum pump 14 can be automatically adjusted by the controller to maintain the proper level of fluid in the degassing vessel 11. If the fluid level in the degassing vessel 11 is near or above the maximum fluid level 26, the pump rates of the fluid pump 12 can be increased, and/or vacuum pump 14 can be reduced. If the fluid level in the degassing vessel 11 is near or below the minimum fluid level 22, the pump rates of the fluid pump 12 can be reduced and/or vacuum pump 14 can be increased.

In certain embodiments, only one sensor is necessary to detect the fluid level in the degassing vessel 11. For example, an ultrasonic sensor or mechanical float can be used to determine the fluid level in the degassing vessel 11. Any other type of fluid level sensor known in the art is contemplated by the first, second and third aspects of the invention.

Carbon dioxide sensor 28 can determine the amount of carbon dioxide present in the dialysate flow path after dialysate has passed through the degasser. The pump rates of fluid pump 12 and vacuum pump 14 can be adjusted as discussed below in response to signals received from the carbon dioxide sensor 28 in order to remove more or less carbon dioxide from the dialysate, and therefore deliver more or less carbon dioxide to the main dialysate flow path. The pumps can be adjusted automatically if the level of carbon dioxide detected in the dialysate by carbon dioxide sensor 28 is higher or lower than a pre-set value. Alternatively, the pumps can be adjusted manually in response to output from the carbon dioxide sensor 28. The system can control the degasser to maintain a carbon dioxide level in fluid exiting the degasser between any of 50 and 200 mmHg partial pressure, 50 and 120 mmHg partial pressure, 50 and 80 mmHg partial pressure, 70 and 100 mmHg partial pressure, 80 and 120 mmHg partial pressure, 50 and 200 mmHg partial pressure, or 100 and 200 mmHg partial pressure. The carbon dioxide sensor 28 can be placed anywhere in the dialysate flow path, but preferably between the outlet of the degassing flow path and the inlet of the dialyzer (not shown). One of skill in the art will understand that the carbon dioxide sensor 28 can be any components capable of measuring the carbon dioxide in a fluid, directly or indirectly.

Carbon dioxide sensors and sensors are known in the art. Examples include non-dispersive infrared (NDIR) detectors that detect carbon dioxide concentration in a gas and which are commercially available from a number of manufacturers, for example Gas Sensing Solutions, Glasgow Scotland; colorimetric optical detectors that detect carbon dioxide in a liquid by means of a substrate that produce color change when the concentration of carbon dioxide in the liquid changes (PreSens Precision Sensing GmbH, Regensburg Germany); and sensors that utilize Severinghaus electrodes, such as the InPro $CO_2$ sensor from Mettler Toledo, Leicester England.

The pumps of the degassing module can be of any type known in the art. In certain embodiments, fluid pump 12 and vacuum pump 14 can be the same type of pump. Alternatively, fluid pump 12 and vacuum pump 14 may be different types of pumps. In certain embodiments, the fluid pump 12 and vacuum pump 14 can be a gear pump. Alternatively, fluid pump 12 and vacuum pump 14 can be a peristaltic pump, a diaphragm pump or an impeller pump. Fluid pump 12 can also have a sensor 31 attached to the fluid pump 12 to monitor performance of the fluid pump 12 and detect wear. The fluid pump 12 must be selected for operating with the pump inlet at a low absolute pressure necessary to efficiently remove carbon dioxide.

Flow of fluid through the degassing module can be variable. Control over the flow can be provided by fluid pump 12. Under certain operating conditions the flow rate provided by fluid pump 12 can be less than the flow rate through the main dialysate loop. Fluid pump 12 can be operated so that flow through the degassing module is significantly greater than flow through the main dialysate loop. Fluid pump 12 can be operated to move fluid through the degassing flow loop at a rate of 2-3 times that of the dialysate flow path. Alternatively, the fluid pump 12 can be operated to move fluid through the degassing flow loop at a rate between 1-6 times that of the dialysate flow path, 1-2 times that of the dialysate flow path, 3-4 times that of the dialysate flow path, 4-5 times that of the dialysate flow path or 5-6 times that of the dialysate flow path. The flow through the degassing module can be controlled automatically by a controller in communication with the fluid pump 12 depending on the amount of carbon dioxide that is to be removed.

The invention can utilize the vacuum pump 14 to remove gas from the degassing vessel 11 to the atmosphere when the degassing vessel 11 is operated under vacuum. Known degassing systems pump fluid into a vessel at ambient pressure where bubbles are allowed to escape. However, providing a second pump or any one of the specific pump configurations described in the first, second and third aspects of the invention to keep a degassing vessel 11 under vacuum can unexpectedly result in higher amount of gases such as carbon dioxide being removed.

The passage from the degassing vessel 11 to vent valve 10 can be covered by a hydrophobic membrane (not shown). A hydrophobic membrane will prevent fluid from escaping the degassing vessel 11 through mechanical vent valve 20. This, in turn, protects the vacuum pump 14 from being damaged by liquid and prevents undesired loss of liquid from the system while still enabling gas to be removed. The hydrophobic membrane can be positioned in any appropriate location to guard against inadvertent fluid flow to the vacuum pump 14, and thereby prevent fluid damage. One example of a hydrophobic membrane is Polytetrafluoroethylene, or PTFE. However, the hydrophobic membrane can be made of any material.

Figure 1B:
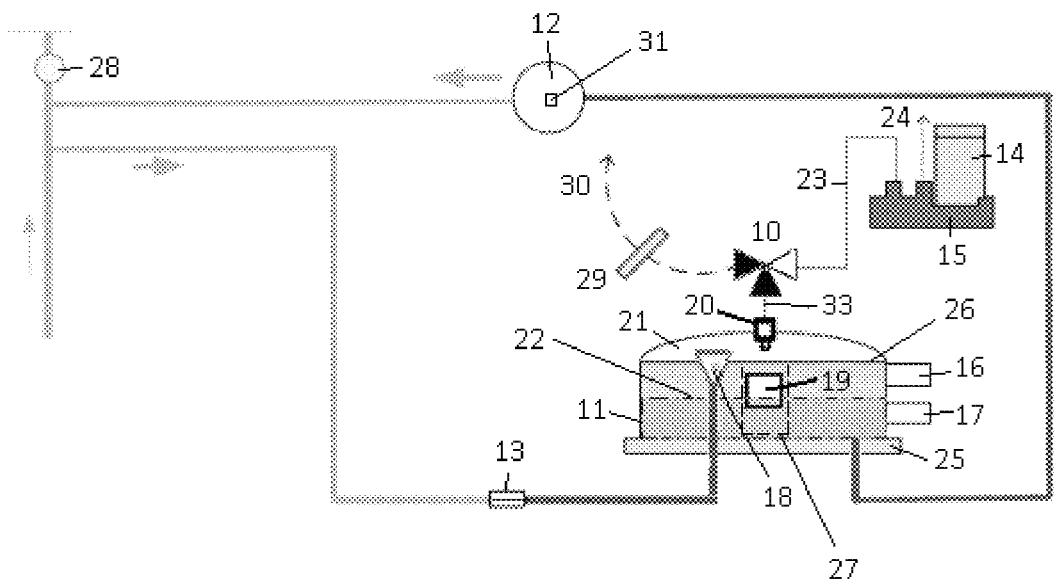
FIG. 1B shows a schematic of a degassing module for use in sorbent dialysis configured to allow air to be drawn into the system.

During draining of the dialysis system of the first, second and third aspects of the invention, air can be drawn into the system in order to drain out the fluid in the fluid pathways of the system. Air can be added to the system through vent valve 10 as shown in FIG. 1B. In FIG. 1B, the pathways of vent valve 10 that are open are shown in black. Air can be passed through filter 29, which can remove any particulate matter and microorganisms before the air enters the dialysis system, and into the degassing vessel 11 through vent valve 10. Fluid pump 12 can force this air into the dialysate flow path (not shown).

Figure 2:
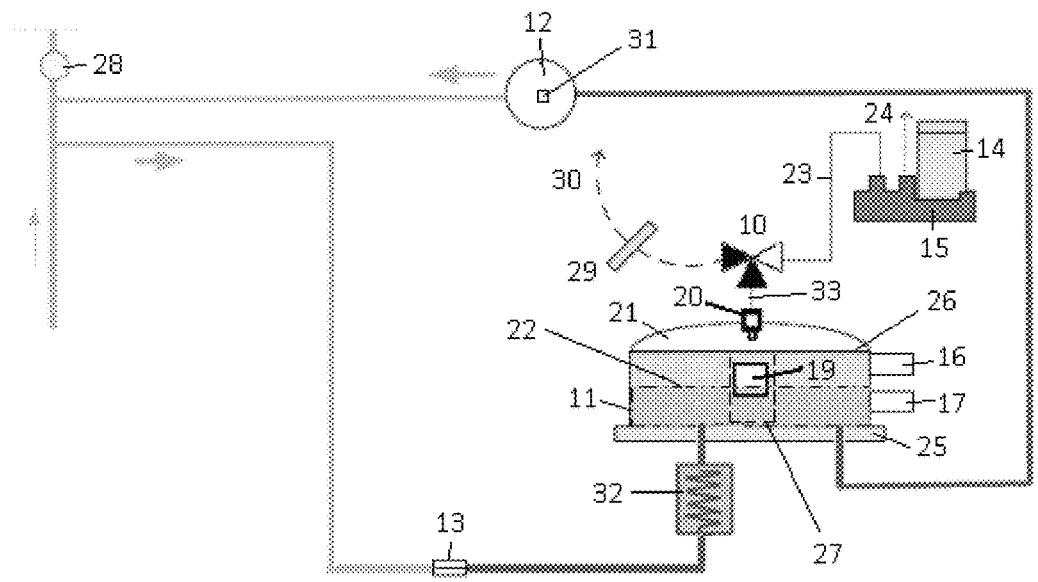
FIG. 2 shows a schematic of a degassing module for use in sorbent dialysis configured to degas dialysate utilizing a nucleation chamber.

As shown in FIG. 2, the function of the degas sprayer can be replaced by a nucleation chamber 32. Nucleation chamber 32 contains a high surface area medium, such as fiber mesh, filter or beads, or other configuration known to those of ordinary skill. The high surface area provides sites where gas bubbles can nucleate and collect to form larger bubbles, making removal of the gases more efficient. The bubbles rise through the fluid as the fluid enters the degassing vessel 11 and collect at the gas space 21, similar to what is shown in FIG. 1A. The nucleation chamber 32 can be placed inside of the degassing vessel 11, so that fluid moves through the nucleation chamber 32 as the fluid moves through the degassing vessel 11 and gas bubbles, once freed from the high surface area medium in the nucleation chamber 32, are immediately collected in the gas space 21 of the degassing vessel 11.

In certain embodiments, both a nucleation chamber and a degas sprayer can be used. Such an arrangement can further help gas to be released from solution to collect at the top of the degassing vessel 11. However, in certain embodiments, only one of a degas sprayer or nucleation chamber can be used.

Figure 3:
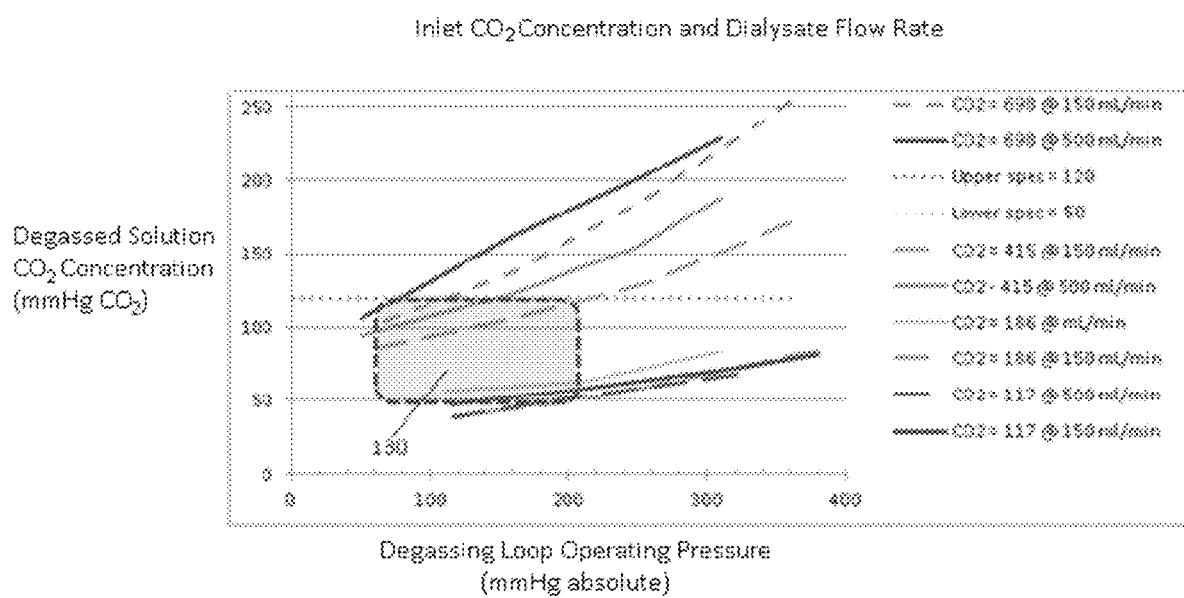
FIG. 3 is a graph showing the outlet $CO_2$ concentration in a degasser as a function of the absolute pressure in the degassing vessel.

FIG. 3 is a graph showing the $CO_2$ outlet concentration, stated as partial pressures, at the outlet of the degasser as a function of the absolute pressure in the degassing vessel 11 for a variety of $CO_2$ inlet concentrations, stated as partial pressures. The block labeled 130 is a desired operating $CO_2$ concentration, expressed as a partial pressure, of between 50 and 120 mmHg. The absolute pressure in the degassing vessel 11 shown in FIGS. 1 and 2 is a function of the fluid pressure, determined by the pump rate of the fluid pump 12, and the vacuum pressure, determined by the pump rate of the vacuum pump 14. By controlling the two pumps, the pressure in the degassing vessel 11 can be accurately controlled. As shown in FIG. 3, the degasser of the first, second and third aspects of the invention is capable of removing enough $CO_2$ to maintain a carbon dioxide level at the outlet of the degasser between 50 and 120 mmHg for a large range of inlet $CO_2$ concentrations and dialysate flow rates. A degassing vessel pressure of between 60 and 200 mmHg absolute pressure can allow for optimal $CO_2$ removal across a range of inlet $CO_2$ concentrations and dialysate flow rates. In certain embodiments, degassing vessel pressure of between any of 40 mmHg and 2000 mmHg, 40 mmHg and 300 mmHg, 40 mmHg and 100 mmHg, 80 mmHg and 150 mmHg, 120 mmHg and 250 mmHg or 200 mmHg and 300 mmHg, can allow for optimal $CO_2$ removal. The desired outlet concentration of $CO_2$ can be obtained for the entire range of inlet $CO_2$ concentrations and flow rates tested by adjusting the pump rates of the two pumps to arrive at the necessary degassing vessel pressure. The vacuum pump 14 may be shut off if the $CO_2$ concentration is below the lower limit. In such cases, the pressure in the degassing vessel 11 will be the same as the pressure of the dialysate fluid, which can be up to 2000 mmHg.

Figure 4:
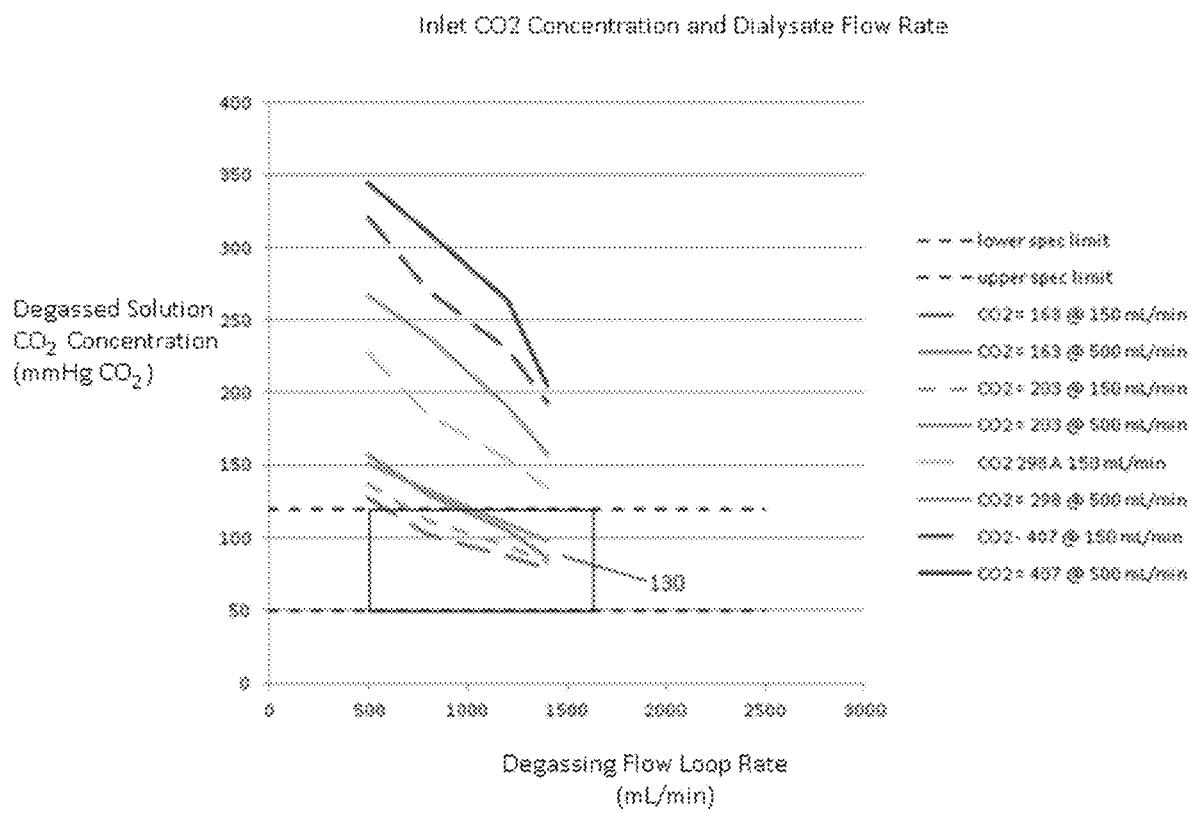
FIG. 4 is a graph showing the outlet $CO_2$ concentration in a degasser as a function of the flow rate in a system with a degasser at ambient pressure.

FIG. 4 provides comparative data for known systems operating at ambient pressures showing an outlet $CO_2$ concentration, stated as partial pressure, in a system that does not use a vacuum pump as in the first, second and third aspects of the invention. Because no vacuum pump is used in known systems, and the known degassing vessels are not able to operate at low absolute pressures, the amount of $CO_2$ removed is limited by the need to maintain sufficient pressure in the degassing vessel to vent the released gas. As can be seen in FIG. 4, a degasser without a degassing vessel under vacuum can only operate to obtain an outlet $CO_2$ concentration of between 50 and 120 mmHg when the inlet concentration of $CO_2$ is around 200 mmHg or below.

Figure 5A:
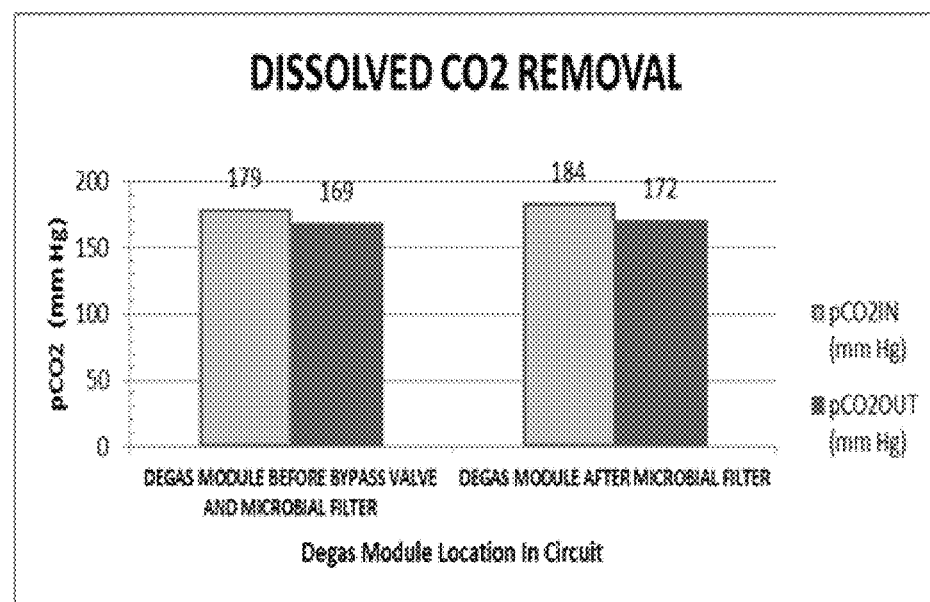
FIG. 5A is a graph showing the amount of dissolved $CO_2$ removed by a degasser with a fluid pump upstream of the degassing vessel for two locations in a dialysis circuit.
Figure 5B:
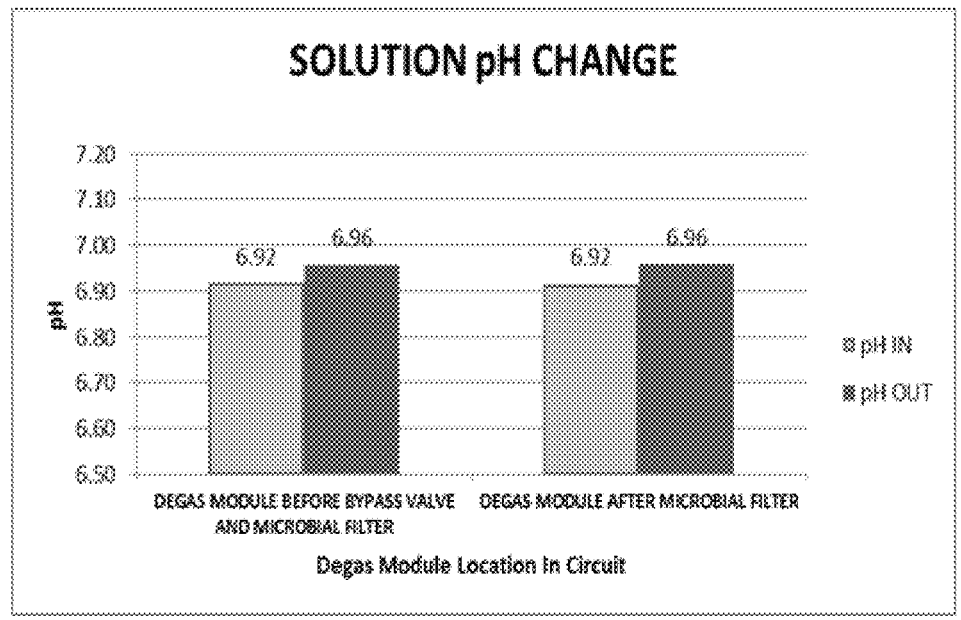
FIG. 5B is a graph showing the change in pH of a fluid passing through a degasser with a fluid pump upstream of the degassing vessel for two locations in a dialysis circuit.
Figure 6A:
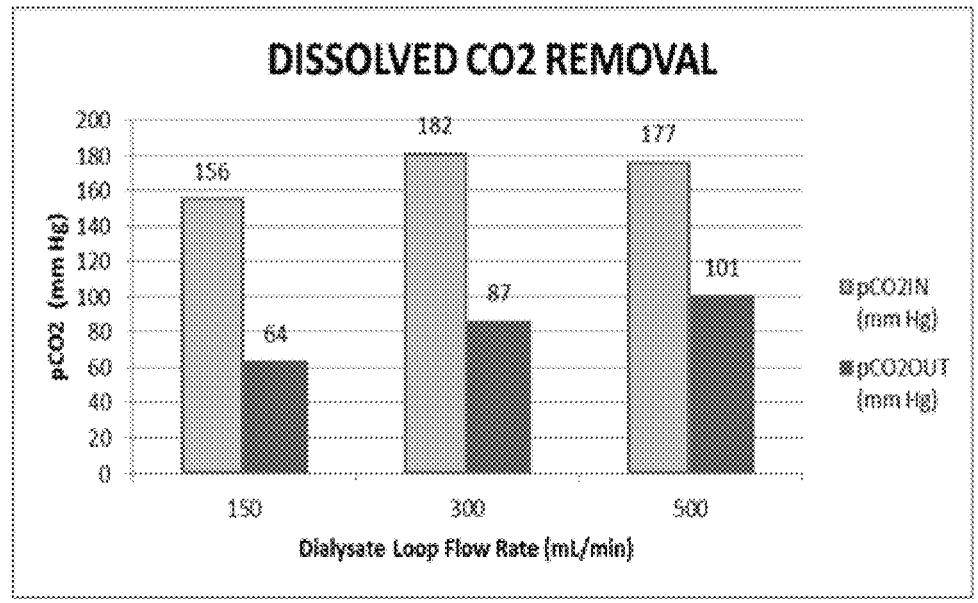
FIG. 6A is a graph showing the amount of dissolved $CO_2$ removed by a degasser with a fluid pump downstream of the degassing vessel as a function of the dialysate flow loop flow rate.
Figure 6B:
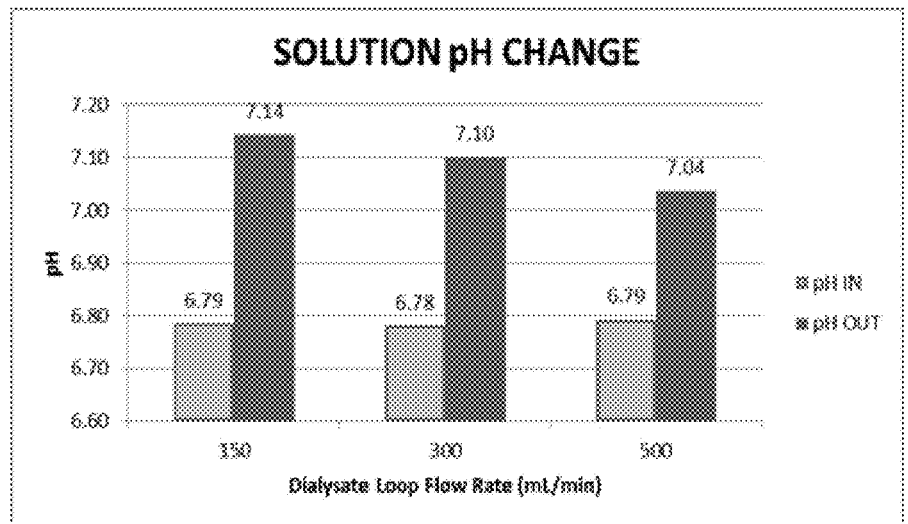
FIG. 6B is a graph showing the change in pH of a fluid passing through a degasser with a fluid pump downstream of the degassing vessel as a function of the dialysate flow loop flow rate.

As shown in FIGS. 5 and 6, the addition of the fluid pump downstream from the degassing vessel can be important to the first, second and third aspects of the invention. By placing the fluid pump downstream of the degas vessel, the efficiency of removing $CO_2$ was increased. FIG. 5A shows the amount of $CO_2$ removed from dialysate without operating the degas vessel under vacuum by means of a fluid pump placed downstream of the degas vessel. FIG. 5B shows the change in pH in the same system. By contrast, FIGS. 6A and 6B show the amount of $CO_2$ removed, and the effect on pH, in the same system with a fluid pump added downstream of a degassing vessel, shown for a dialysate flow path flow rate from 150 mL/min to 500 mL/min. As can be seen in FIGS. 6A and 6B, by adding the fluid pump to a downstream location, between 1/3 and 2/3 of $CO_2$ can be removed, depending on the dialysate flow rate. By contrast, as shown in FIGS. 5A and 5B, much less $CO_2$ is removed when the fluid pump is placed upstream of a degas vessel.

As can be seen in FIG. 5, the location of the degasser upstream or downstream with respect to a microbial filter does not alter the amount of $CO_2$ removed. The described configuration with degasser upstream of the microbial filter can provide for the removal of gas from the dialysate prior to reaching the microbial filter, and thereby advantageously reduce gas accumulation in the microbial filter.

Figure 7:
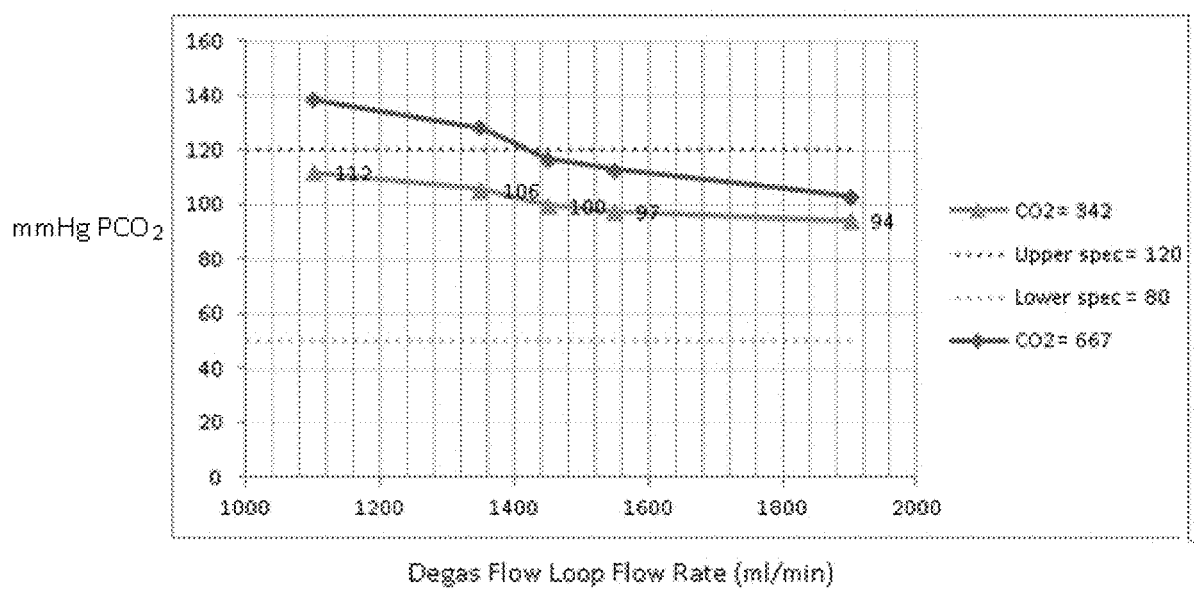
FIG. 7 is a graph showing the amount of dissolved $CO_2$ removed by a degasser with a fluid pump downstream of the degassing vessel as a function of the degassing flow loop flow rate.

FIG. 7 shows the amount of $CO_2$ removed as a function of the rate of flow through the degassing flow loop. In all runs shown in FIG. 7 the dialysate flow rate was 600 mL/min. As is shown, the amount of $CO_2$ removed can increase as the flow rate through the degassing flow loop increases.

Figure 8A:
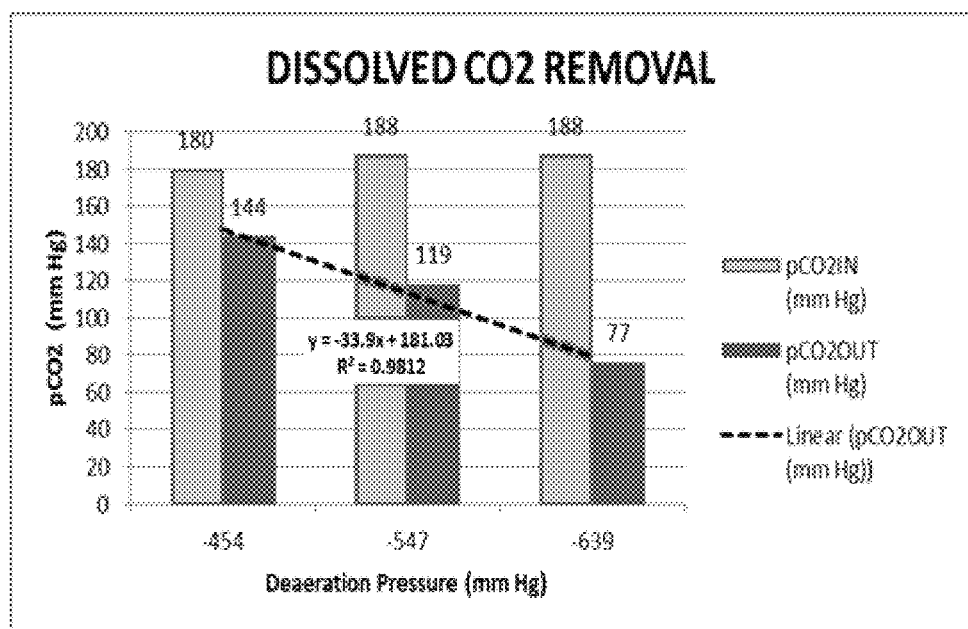
FIG. 8A is a graph showing the amount of dissolved $CO_2$ removed by a degasser with a fluid pump downstream of the degassing vessel as a function of the vacuum level in the degassing flow loop.
Figure 8B:
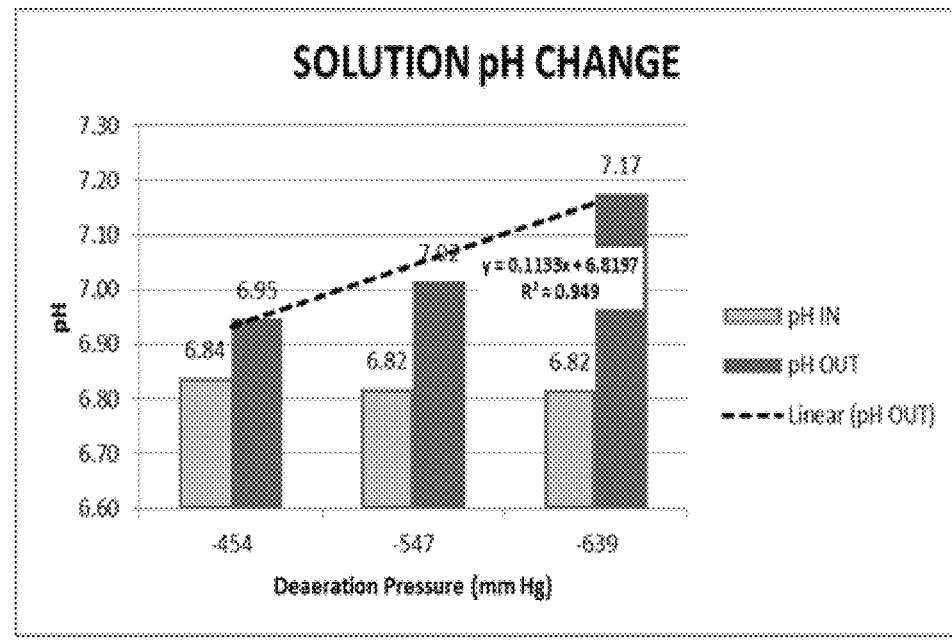
FIG. 8B is a graph showing the change in pH of a fluid passing through a degasser with a fluid pump downstream of the degassing vessel as a function of the vacuum level in the degassing flow loop.

FIGS. 8A and 8B show the amount of $CO_2$ removed, and the effect on pH, as a function of the absolute pressure in the degassing flow loop. In these trials, the dialysate flow rate and degassing flow rate were held constant at 300 mL/min. As can be seen, more $CO_2$ is removed as the absolute pressure in the degassing flow loop is reduced. As is shown in FIGS. 8A and 8B, the degassing flow loop pressure can have a linear relationship with outlet $CO_2$ concentration. The pressure in the degassing flow loop, and in the degas vessel in particular, can be affected by the action of the fluid pump pulling fluid through the degas flow restrictor and the vacuum pump acting to remove the released gases from the degassing vessel. The action of the vacuum pump allows released gases to be vented from the degas vessel when the degas vessel is operated at pressures substantially below ambient. This, in turn, can allow for the removal of additional $CO_2$.

Figure 9A:
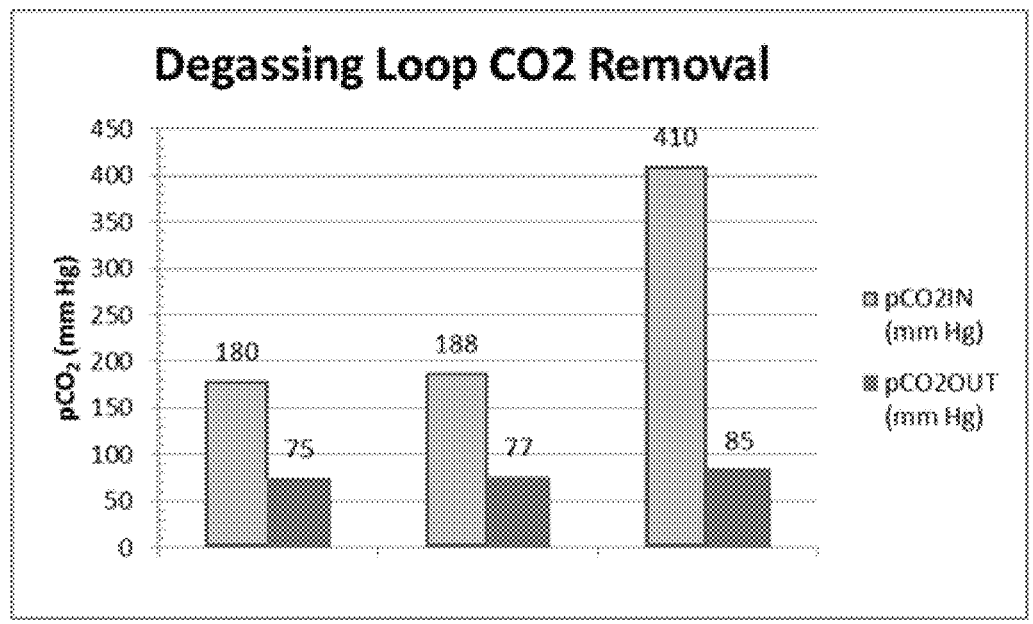
FIG. 9A is a graph showing the amount of dissolved $CO_2$ removed by a degasser with a fluid pump downstream of the degassing vessel as a function of the $CO_2$ concentration at the inlet of the degasser.
Figure 9B:
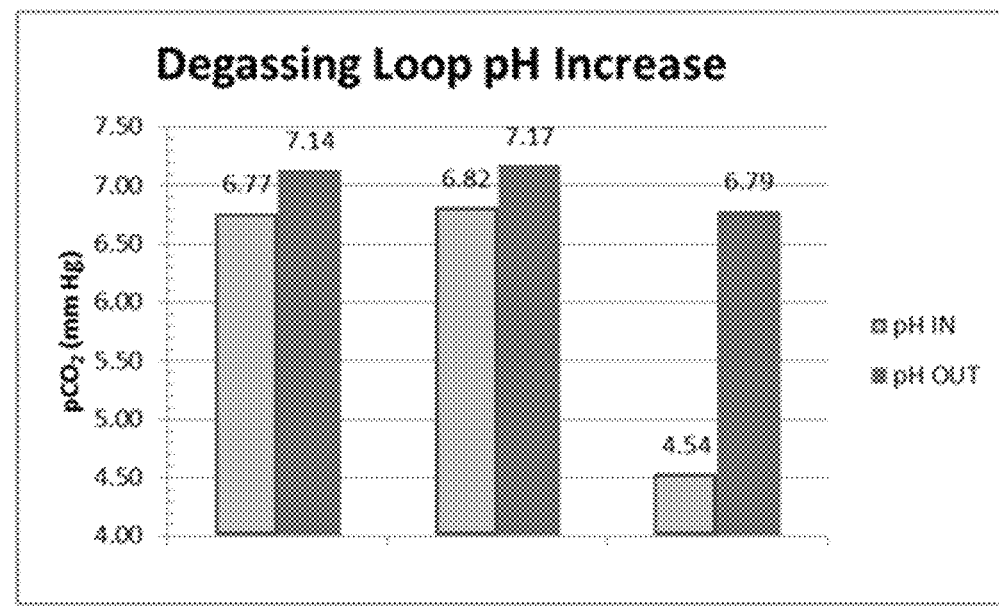
FIG. 9B is a graph showing the change in pH of a fluid passing through a degasser with a fluid pump downstream of the degassing vessel as a function of the pH at the inlet of the degasser.

The outlet $CO_2$ concentration can be dependent on the inlet $CO_2$ concentration, the fluid pressures within the degassing flow loop, and the rates of flow through dialysate flow path and the degassing flow loop. The dialysate flow path and the degassing flow loop can operate in parallel or in series. FIGS. 9A and 9B show the amount of $CO_2$ removed, and the effect on pH with differing inlet $CO_2$ concentrations. In all trials, the flow rates through the dialysate flow path and degassing flow loop were held at 300 mL/min and the degassing loop fluid pressure was held constant at 630 mmHg vacuum. As can be seen, the outlet $CO_2$ concentration is not significantly affected by large changes in the inlet $CO_2$ concentration. In all cases, the outlet $CO_2$ concentration was reduced to between 75-85 mmHg, despite the variations in inlet $CO_2$ concentrations.

Figure 10:
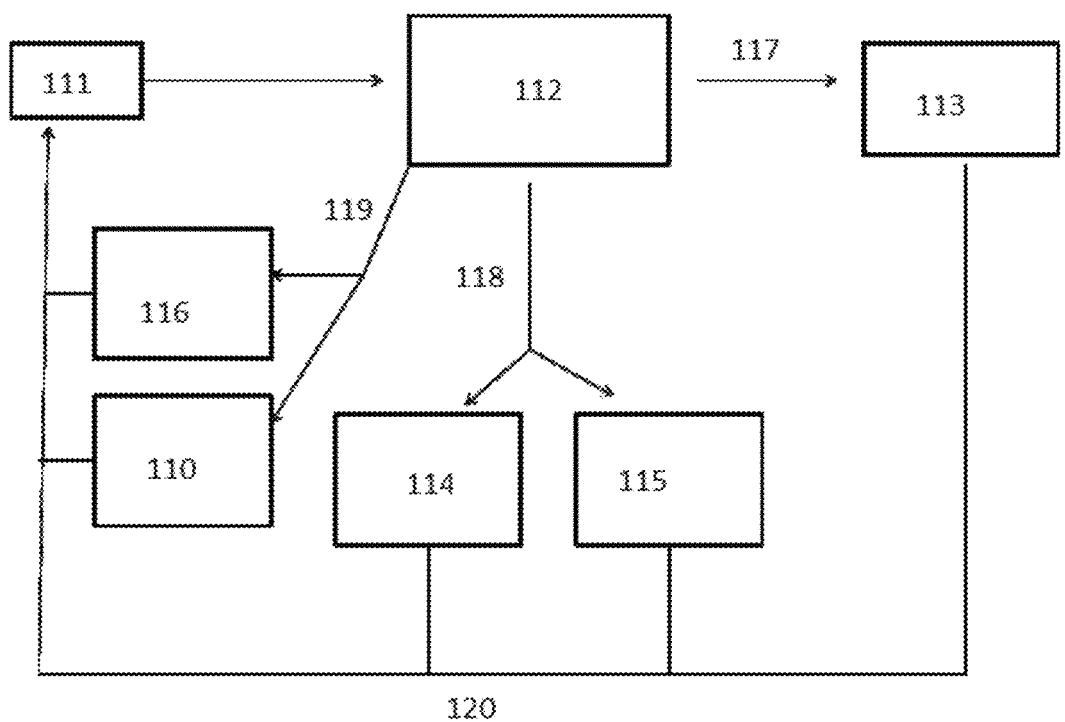
FIG. 10 is a flow diagram showing the operation of the pumps in relation to the carbon dioxide present in the dialysate.

FIG. 10 shows a flow diagram, explaining one non-limiting embodiment of the operation of the vacuum pump and fluid pump of the first, second and third aspects of the invention in relation to the data received from the $CO_2$ sensor. In FIG. 10, both the vacuum pump and the liquid pump may be operated simultaneously. Data received from the $CO_2$ sensor 111 is transmitted to controller 112. If the $CO_2$ concentration detected by the $CO_2$ sensor 111 is within the desired range in step 117, the controller 112 can continue operating the pumps in the same manner in step 113. If the $CO_2$ concentration detected by the $CO_2$ sensor 111 is too low 118, the controller 112 can do either of two options. The controller 112 can cause the fluid pump to decrease the flow rate in the degassing flow loop in step 114, causing the absolute pressure of the fluid in the degassing loop to increase and thereby reduce the amount of $CO_2$ removed by the degasser as shown in FIGS. 3 and 7. Step 114 can alternatively involve that the fluid pump is shut off completely, thereby stopping the removal of $CO_2$ from the dialysate. Alternatively, the controller 112 can decrease the pump rate of, or shut off completely, the vacuum pump in step 115. In certain embodiments, both steps 114 and step 115 can be carried out in response to a signal showing the $CO_2$ level to be too low. Decreasing the pump rate of the vacuum pump, or shutting the vacuum pump off completely, will result in less gas being removed from the degas vessel. If the $CO_2$ concentration detected by the $CO_2$ sensor 111 is too high 119, the controller 112 can cause the fluid pump to increase the flow rate through the degassing flow loop in step 116, and thereby increase the amount of $CO_2$ removed by the degasser as shown in FIGS. 3 and 7. The controller 112 can increase the pump rate of the vacuum pump in step 110, to remove the increased amount of gas being released from solution when the flow rate through the fluid pump is increased 116 which also enables the proper liquid level to be maintained in the degas vessel when the pressure within the degas vessel is reduced and causes the removal of more $CO_2$. Steps 116 and 110 can both be carried out in response to a signal showing that the $CO_2$ concentration is too high. Regardless of the action taken in response to the data received by the $CO_2$ sensor 111, the $CO_2$ concentration in the dialysate can be continuously monitored, as represented by arrow 120, and further adjustments to the rate of the fluid pump can be made as the $CO_2$ concentration in the dialysate changes. The vacuum pump may run continuously with the exception of step 115, to draw out the $CO_2$ from the degas vessel as the $CO_2$ accumulates.

Figure 11:
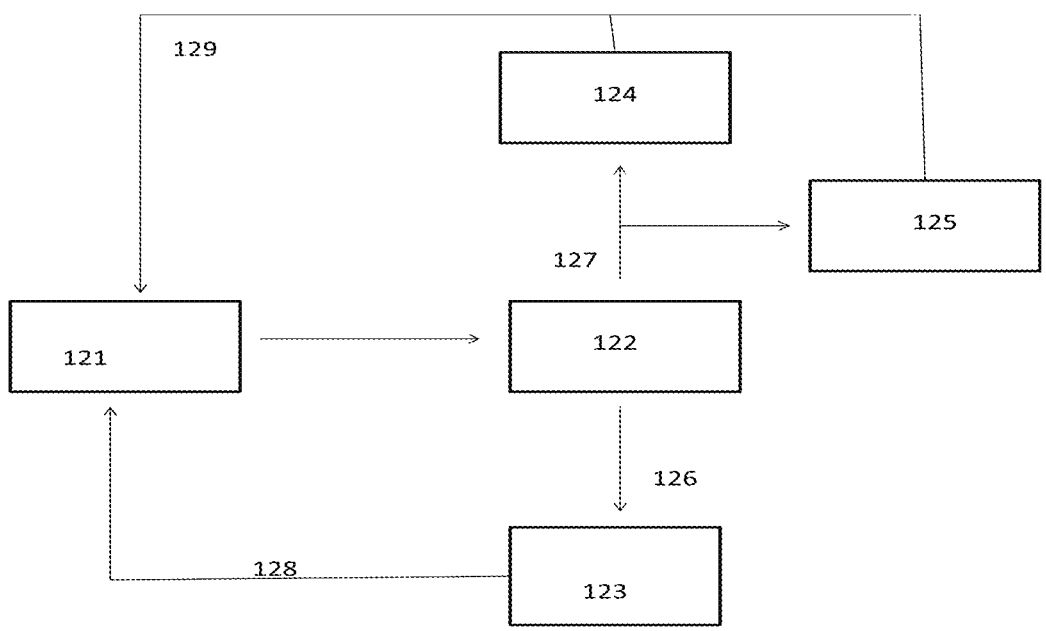
FIG. 11 is a flow diagram showing an alternative operation of the pumps in relation to the carbon dioxide present in the dialysate.

FIG. 11 shows an alternative embodiment to that shown in FIG. 10, where the vacuum pump and fluid pump are run alternately. The fluid pump can be operated to pull fluid through the degassing flow loop. Data is sent from the $CO_2$ sensor 121 to the controller 122 showing the $CO_2$ concentration in the dialysate. While the $CO_2$ concentration in the dialysate is above the desired range 123, the fluid pump can be operated as explained above to remove $CO_2$ from the dialysate. The $CO_2$ concentration can be continuously monitored as the fluid pump operates, as shown by arrow 128. Once the $CO_2$ concentration has decreased into the desired range 127, the controller 112 can cause the fluid pump to shut off 124. Simultaneously, the vacuum pump can be turned on 125 to remove the gases that have collected in the degas vessel. While the fluid pump is shut down, the $CO_2$ concentration in the dialysate will increase, due to the fact that dialysate is not being directed through the degasser, and will be monitored as shown by arrow 129. When the $CO_2$ concentration has risen 126 to a desired range 123, the fluid pump can again be operated and the vacuum pump shut off.

The controller can set initial pump rates for both the vacuum pump and fluid pump based on the initial carbon dioxide concentration in the dialysate. For example, if the initial carbon dioxide concentration in the dialysate is 415 mmHg partial pressure, the fluid pump and vacuum pump may be set to maintain an absolute pressure in the degas vessel of 100 mmHg. As shown in FIG. 3, this would allow for an outlet $CO_2$ concentration of between 50-120 mmHg partial pressure. If, during operation, the concentration of carbon dioxide were to become reduced to 117 mmHg partial pressure, the controller can alter the pump rates of the fluid pump and/or vacuum pump as described above to maintain an absolute pressure in the degas vessel of 190 mmHg. As shown in FIG. 3, this would maintain a carbon dioxide level above 50 mmHg partial pressure.

In certain embodiments, the degasser can be located in a fluid flow path in a position directly after the sorbent cartridge. The position of the degasser, however, is not limited to any one position. Alternatively, the degassing module may be located in other positions between the sorbent cartridge and the dialyzer.

To make use of the dialysis system of the first, second and third aspects of the invention easier, the valves and pumps may be operated by a programmable controller or computer system that can be programmed to regulate flow through the pumps and valves and into and out of the reservoirs. A rotometer or turbine with optical sensor, photocell, magnetic sensor, or other flow sensing apparatus may detect the flow of fluid through any two points in the degassing system. For example, an optical fluid flow device can be provided for measuring flow wherein the device includes an optical fluid pressure measuring device having sensors positioned in any one of the flow paths between the reservoirs, in the connectors, or in the valves or valve assemblies. The optical fluid sensors described above can be connected to an interferometer associated with an opt-electronic demodulator which has an output signal representing the differential pressure between the two sensed areas. In certain embodiments, a flow sensing apparatus can have a flow-responsive element projecting into a fluid flow path, and a position sensor associated with the element which detects a change in position of the flow-responsive element in response to the fluid flow. The flow-responsive element can be made of a wide variety of materials having the desired properties known to those of ordinary skill in the art.

The reader is directed to FIG. 8A, which demonstrates the relationship between the pressure in the degasser and the concentration of dissolved carbon dioxide in the fluid that has passed through the degasser, and also to FIG. 9A, which demonstrates that the carbon dioxide concentration in the fluid that has passed through the degasser remained constant in a tight range when the carbon dioxide concentration in the fluid entering the degasser was more than doubled. As illustrated in FIG. 8A and FIG. 9A, the operating pressure of the degasser can be used to control the concentration of carbon dioxide in the fluid exiting the degasser.

Figure 12:
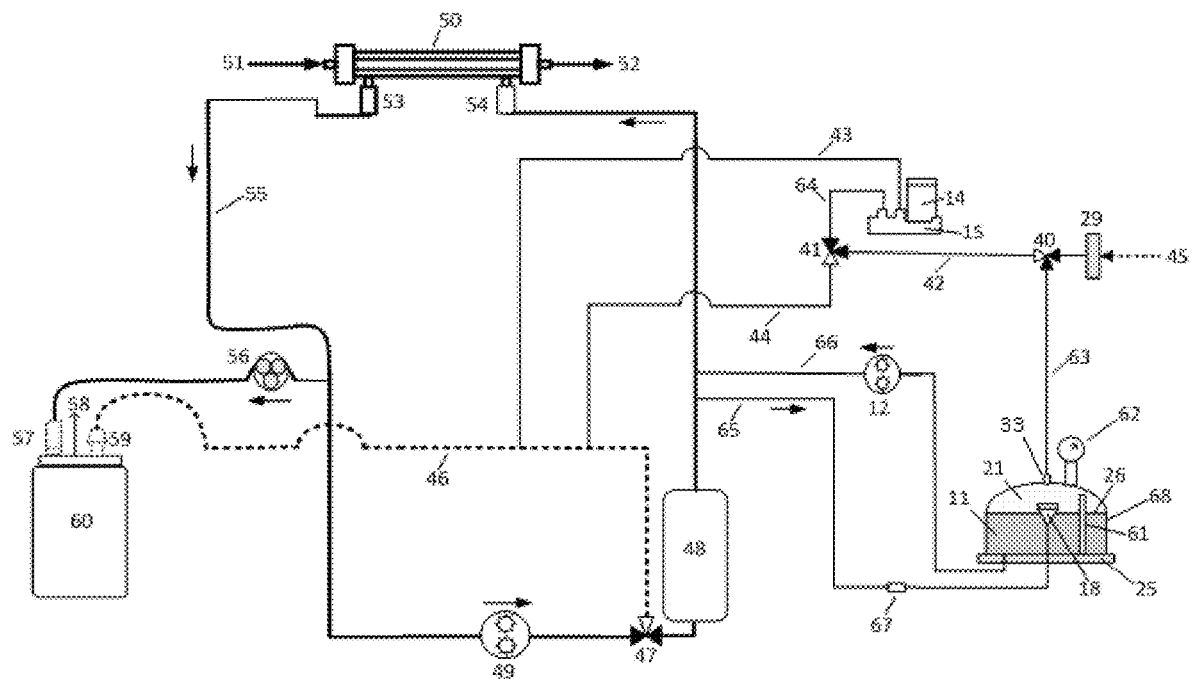
FIG. 12 is a schematic of a degassing system having a pressure sensor to measure the pressure within the degasser; and having control valves to alternately connect the vent port of the degassing vessel to an air inlet filter, a drain line for gas removal through a vacuum pump, or a dialysate flow path for recirculation of fluid.

Referring to FIG. 12, a description is provided of how the concentration of dissolved carbon dioxide in the dialysate can be controlled by controlling the operating fluid pressure in the degasser to a predetermined level. Blood enters dialyzer 50 as shown by arrow 51 and exits the dialyzer 50 as shown by arrow 52. Dialysate recirculating in dialysate flow path 55 enters the dialyzer 50 at connector 54 and exits the dialyzer 50 at connector 53 with urea that has been removed from the blood. The dialysate is pumped by dialysate pump 49 through drain valve 47 and through sorbent cartridge 48 where the urea is removed from the dialysate by an exchange process that results in carbon dioxide being added to the dialysate as the dialysate flows through sorbent cartridge 48. The dialysate exiting the sorbent cartridge 48 is drawn into the degassing system by action of fluid pump 12 through inlet line 65. The dialysate passes through degas flow restrictor 67 where the fluid pressure is reduced by the pressure drop that occurs as the dialysate flows through the degas flow restrictor 67. The dialysate enters degassing vessel 68 and passes through optional degas sprayer 18 that acts to increase the surface area of the liquid and thereby increase the rate at which the dissolved carbon dioxide is released from the fluid to the gas space 21 at the top of the degassing vessel 68. Carbon dioxide gas is collected in the gas space 21 and the degassed fluid is collected in the liquid space of degassing vessel 11. Gas bubbles in the liquid rise to be collected in gas space 21 and the liquid exits the base 25 of degassing vessel 68 and passes through fluid pump 12 and is returned to the recirculating dialysate flow path 55 through return line 66.

The released gas can exit the degassing vessel 68 at outlet connector 33 and pass through vent line 63 to vent control valve 40 through outflow line 42 to outflow valve 41. During degassing, outflow valve 41 directs the flow path to gas removal pump assembly 15 through gas removal line 64. Vacuum pump 14 pulls the gas from the low pressure environment of degassing vessel 68 and pumps the gas out through degassing outlet line 43. Degassing outlet line 43 can optionally be connected to drain line 46. Connecting degassing outlet line 43 to drain line 46 muffles the noise of the vacuum pump 14 and directs any condensed water vapor to reservoir 60 through drain line 46 and connector 59. The removed gas flows out of reservoir 60 through vent 58.

Level sensor 61 can measure the liquid level 26 in degassing vessel 68. Level sensor 61 can be an ultrasonic sensor. Level sensor 61 can be an array of reed switches that detect the height of a magnetic float. Level sensor 61 can include a linear array of Hall-effect sensors. The rate of vacuum pump 14 can be increased to increase the liquid level 26 when level sensor 61 detects that the liquid level 26 is below a predetermined level. The rate of vacuum pump 14 can be reduced when the level sensor 61 detects that the liquid level 26 is above a predetermined level. The vacuum pump 14 can act as a check valve preventing air or liquid from returning to the degasser through degassing outlet line 43, but can allow gas outflow from the degasser through degassing outlet line 43 including when the gas removal pump is de-energized or turned off. Air can be rapidly evacuated from the dialysate flow path 55 through outlet connector 33, vent line 63, vent control valve 40, degassing outflow valve 41 and gas removal pump assembly 15 and degassing outlet line 43 during priming operations when the liquid entering the dialysate flow path 55 causes the pressure to increase, forcing the air in the gas space 21 of degassing vessel 68 through outlet connector 33 when the pressure in gas space 21 is greater than atmospheric pressure.

Vent control valve 40 can be switched to filter 29 and air can be drawn into the degassing vessel 68 as depicted by arrow 45 when liquid is being drained from the recirculating dialysate flow path 55 through drain valve 47 through drain line 46 and connector 59 to reservoir 60. Filter 29 can have a pore size that excludes microbes and particulate to prevent contamination of the system when air is drawn in.

During flushing, cleaning and disinfection of the dialysis system, degassing vessel 68 can be completely filled with liquid and liquid can be passed out through outlet connector 33 through vent line 63, vent control valve 40, and degassing outflow valve 41 to recirculation line 44. This flow path enables cleaning and disinfection solutions, including the non-limiting examples of hot water, heated citric acid solution, and bleach to be recirculate through the outlet connector 33, vent line 63, and vent control valve 40. In this manner microbiological contamination and biofilms can be minimize in the degassing vessel 68 and also in the flow path used to bring air into the system when liquid is being drained from the system.

The flow restrictor 67 can have a fixed restriction, or can comprise a pressure regulator that changes the amount of flow restriction as the pumping rate of fluid pump 12 changes, such that a predetermined pressure is maintained in the dialysate exiting the restrictor across a range of operating rates of fluid pump 12. The amount of restriction caused by flow restrictor 67 can be controlled to achieve a predetermined pressure in the fluid passing through the degasser.

Pressure sensor 62 can measure the fluid pressure in the degassing system. Pressure sensor 62 can be located on the degassing vessel 11 and can measure the pressure in the liquid or the gas. Pressure sensor 62 can be located at any point in the degasser between the flow restrictor 67 and fluid pump 12. The pressure measurement obtained from pressure sensor 62 can be used to adjust the restriction of flow restrictor 67 to obtain a predetermined pressure in the degassing system. The rate of fluid pump 12 can be controlled to achieve a predetermined fluid pressure in the degassing system. The rate of fluid pump 12 can be increased to reduce the fluid pressure in the degasser if the fluid pressure measured by pressure sensor 62 is above the predetermined pressure. The rate of fluid pump 12 can be decreased to increase the fluid pressure in the degasser if the fluid pressure measured by pressure sensor 62 is below the predetermined fluid pressure.

In FIG. 12, an alternative control scheme can be employed in any embodiment of the invention, wherein the pressure in the gas space 21 can be controlled by vacuum pump 14. The pressure in the gas space 21 can be measured by pressure sensor 62 and a controller can adjust the rate of vacuum pump 14 to keep the pressure in gas space 21 at a predetermined level. In this alternative control scheme, the rate of fluid pump 12 can be increased to decrease the liquid level 26 in degassing vessel 68 or the rate of fluid pump 12 can be decreased to increase the liquid level 26 in degassing vessel 68. In this scheme, liquid level measurements from level sensor 61 can be used to determine whether the rate of fluid pump 12 should be increased or decreased. Those of skill in the art will note that the rate of fluid pump 12 can be maintained at a constant rate while increasing the amount of flow restriction caused by flow restrictor 67 to decrease the liquid level 26 in degassing vessel 68 or decreasing the amount of flow restriction caused by flow restrictor 67 to increase liquid level 26 in degassing vessel 68.

Figure 13:
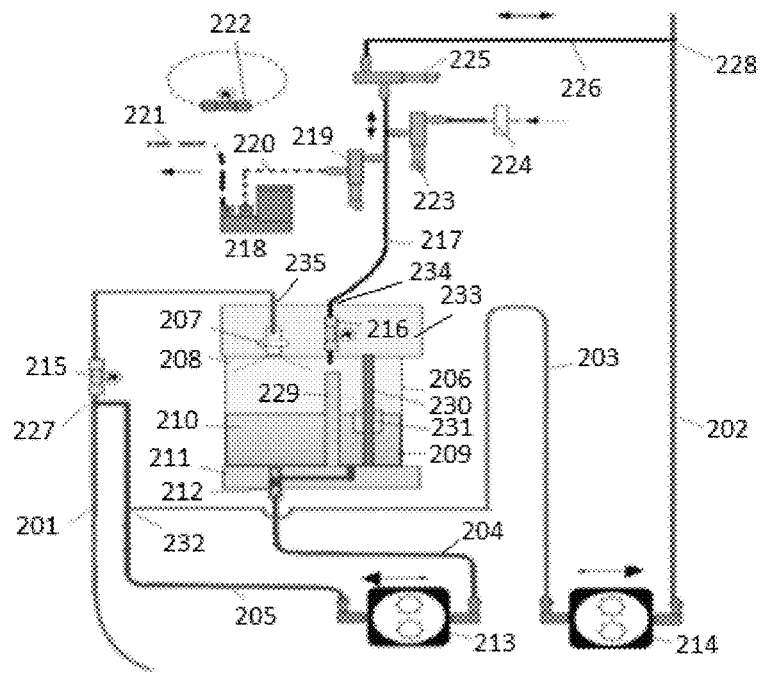
FIG. 13 shows a degassing vessel with a degas sprayer entering through a top of the degassing vessel.

FIG. 13 is an alternative degassing system for use in dialysis that reduces foaming. During treatment, dialysate is pumped from a dialyzer (not shown) through dialysate line 201. Dialysate can enter degassing vessel 206 through a fluid inlet 235 and into degas sprayer 207, which enters the degassing vessel 206 through a top 233 of degassing vessel 206. In certain embodiments, a fluid inlet (not shown) can be located at the bottom of the degassing vessel 206 or at any other location relative to the degassing vessel 206. The fluid inlet 235 can be fluidly connectable to a dialysate flow path via the dialysate line 201. An internal conduit or passageway can convey the fluid to the degas sprayer 207 at the top 233 of the degassing vessel 206. The top portion 208 of the degassing vessel 206 can also be referred to as the "headspace." The degas sprayer 207 sprays dialysate downwardly into the degassing vessel 206. Foaming can be controlled by spraying downwardly onto a liquid pool in the degassing vessel 206. The downward spray cuts the upward growth of foam, as described. The degassing vessel 206 can be separated into a spray chamber 210 and a float chamber 209 by separator 229. A channel (not shown) can be included in separator 229 to allow fluid to move from the spray chamber 210 to the float chamber 209 to provide an accurate reading on fluid level. Any fluid connections in addition to a channel such as a passageway or other means to equilibrate the fluid level between the spray chamber 210 and a float chamber 209 is contemplated. In a preferred embodiment, the fluid connections connecting the spray chamber 210 and the float chamber 209 are located in a lower portion of the degassing vessel 206. The float chamber 209 can include one or more level sensors. As illustrated in FIG. 13, the level sensor can include a magnetic float 231 on guide 230. A linear array of Hall effect sensors (not shown) can be included to measure the level of the float 231 and determine the fluid level in the degassing vessel 206. In certain embodiments, the float 231 can be magnetic, and a linear array of Hall effect sensors can measure the height of the float directly. Alternatively, a magnet can be affixed to the float 231. In alternative embodiments, the level sensors can include a capacitive or ultrasonic sensor to measure the height of the liquid directly. An ultrasonic sensor emits an ultrasonic wave and measures the distance to the liquid based on the time between emission of the wave and detection of the wave reflected back by the liquid. A capacitive sensor measures distance to the liquid by measuring changes in capacitance as the liquid moves closer to or further away from the sensor. The height of the fluid in the degassing vessel 206 can be controlled to within a predetermined range to ensure that the liquid level is below the degas sprayer 207, ensuring that the degas sprayer 207 nozzle is exposed and that atomized fluid is exposed to the low pressure in the top portion 208 of the degassing vessel 206. The fluid level should also remain low enough that loss of liquid through the gas outlet line 217 is prevented, and high enough such that undissolved gas bubbles in the liquid are separated and captured.

Fluid can be sprayed into the spray chamber 210 of the degassing vessel 206. Gas can be removed from the fluid through a gas outlet 234 fluidly connectable to gas outlet line 217. A gauge pressure sensor 216 in the gas outlet 234 can measure the pressure inside the degassing vessel 206. Gas bubble nucleation can occur as the fluid is sprayed into the spray chamber 210. Before the gas bubbles can exit the degassing vessel 206, the gas bubbles rise through the liquid and are captured and collected in a headspace of the degassing vessel 206. Bubble capture can be ensured when the downward velocity of the liquid in the degassing vessel 206 is less than the rise velocity of the bubbles through the liquid. The degas sprayer 207 atomizes the fluid and creates a high surface area to volume ratio between the liquid droplets and gas in the degas vessel headspace. In certain embodiments, vacuum pump 218 is used to lower the pressure in the degassing vessel 206, and is fluidly connectable to gas outlet line 217 by valve 219 and vacuum line 220 and can be controlled by a controller to maintain a desired pressure within the degassing vessel 206. In a preferred embodiment, the vacuum pump 218 is continuously run at a high rate, and the controller can pulse width modulate valve 219 to control the pressure in the degassing vessel 206 to a desired target. The removed gases are expelled through gas line 221, which can be vented to the air, or alternatively, connected to a waste reservoir.

In a preferred embodiment, the vacuum pump 218 is continuously run at a high rate. Valve 219 is closed when the gas outlet pressure drops below a target pressure and opened when the gas outlet pressure rises above the target pressure. Controlling pressure by only modulating valve 219 maintains the atmosphere within the top portion 208 of the degassing vessel 206 as predominately $CO_2$. Opening vent valve 223 would allow air into the degassing vessel 206, changing the ratio of carbon dioxide, nitrogen, and oxygen in the degassing vessel 206 making control over carbon dioxide difficult. By maintaining a predominately carbon dioxide atmosphere in the degassing vessel 206, the system can precisely control the amount of dissolved carbon dioxide in the dialysate.

Degassed fluid can exit the degassing vessel 206 through a liquid outlet 212 in a base 211 of the degassing vessel 206, fluidly connectable to fluid line 204. The liquid outlet 212 is located at a lower elevation in the degassing vessel 206 than the gas outlet 234 at gas outlet line 217. Fluid can be pumped by fluid pump 213, through fluid line 205, and back to dialysate line 201 at junction 227. The fluid pump 213 provides the force necessary to move fluid from the low pressure degassing vessel 206 to the higher pressure in dialysate line 201. The fluid lines 204, 205, and 201, with degassing vessel 206, form a degassing flow path that is parallel to a main dialysate flow path. Fluid can be pumped from the degassing flow path at junction 232 into the main dialysate flow path through fluid line 203 by dialysate pump 214 into dialysate line 202. The flow rate of fluid through the main dialysate flow path can be controlled by dialysate pump 214, and optionally one or more additional dialysate pumps. As such, the flow rate of fluid through the degassing flow loop can be controlled independently of the flow rate of fluid in the main dialysate flow path. By operating fluid pump 213 at a higher pump rate than dialysate pump 214, fluid can be recirculated through the degassing vessel 206 multiple times prior to returning to the main dialysate flow path, allowing additional control over the amount of gas removed. The rate of liquid recirculation through the degassing vessel 206 can help to ensure sufficient exposure to the headspace of the degassing vessel 206 so that dissolved gases in the liquid come into equilibrium with the gas partial pressures in the degassing vessel 206. In certain embodiments, the flow rate of fluid through the degassing flow loop can be set to about two times the dialysate flow rate. The fluid pump 213 and dialysate pump 214 can be controlled by a controller (not shown) to operate at the desired ratio.

The fluid inlet 235, gas outlet 233, and liquid outlet 212 are each fluidly connectable to the dialysate flow path. In certain embodiments, the fluid inlet 235, gas outlet 233, and liquid outlet 212 can be disconnected from the dialysate flow path to allow the degassing vessel 206 to be removed from the system for maintenance or replacement. The degassing vessel 206 can be reconnected to the system by connecting fluid inlet 235, gas outlet 233, and liquid outlet 212 to lines 201, 217, and 204, respectively. Any method known in the art can be used to fluidly connect fluid inlet 235, gas outlet 233, and liquid outlet 212 to the dialysate flow path, including quick-connect fittings, screw fittings, or any other method or mechanical fastening means.

A vent valve 223 fluidly connected to the gas outlet line 217 can be controlled to allow air into the degassing vessel 206 when the degassing vessel 206 is drained. Filter 224 prevents contamination of the degassing vessel 206, and can have a pore size that excludes microbes and particulate matter to prevent contamination of the system when air is drawn in through vent valve 223. During flushing, cleaning and disinfection of the dialysis system, degassing vessel 206 can be completely filled with liquid and liquid can be passed out through gas outlet line 217 through valve 225 and fluid line 226, to dialysate line 202 at junction 228. The flow path enables cleaning and disinfection solutions, including the non-limiting examples of hot water, heated citric acid solution, and bleach to be recirculate through all of the lines of the degassing system. In this manner, microbiological contamination and biofilms can be minimized in the degassing vessel 206 and also in the flow path used to bring air into the system when liquid is being drained from the system. A temperature sensor (not shown) can be included to monitor the temperature during disinfection, and to measure the temperature of dialysate prior to reaching a heater (not shown) in the dialysate flow path. An ambient pressure sensor 222 can measure the atmospheric pressure outside of the degassing system, and is used conjunction with gauge pressure sensor 216 to determine the absolute pressure in the headspace, or top portion 208 of the degassing vessel 206.

During treatment, the degassing system should control carbon dioxide removal to maintain a carbon dioxide level within a desired range. In certain embodiments, the desired range can be from 40 mmHg-150 mmHg $pCO_2$. The concentration of the dissolved gases in the dialysate exiting the degassing vessel 206 are proportional to the absolute partial pressures of the gas in the top portion 208, and as such, the environmental pressure as measured by ambient pressure sensor 222 can be used to control the gas pressure within the degassing vessel 206. Ambient pressure sensor 222 measures the absolute pressure of the environment outside of the degassing vessel 206. Gauge pressure sensor 216 measures a gauge pressure referenced to the ambient pressure sensor 222. The pressure as measured by ambient pressure sensor 222 plus the gauge pressure measured by gauge pressure sensor 216 provides the absolute pressure in the top portion 208 of the degassing vessel 206. Alternatively, the gauge pressure sensor 216 can be replaced by an absolute pressure sensor to measure the absolute pressure in the headspace, or top portion 208 of the degassing vessel 206, and the ambient pressure sensor 222 is not required. The dialysate flow rate also controls the amount of gas removed. In certain embodiments, the dialysate flow rate through the degassing flow loop can be from 100 mL/min to 800 mL/min. In certain embodiments, the dialysate flow path can include a heater (not shown) to heat the dialysate to a desired temperature prior to reaching the dialyzer. The degassing flow loop can be positioned either upstream or downstream of the heater. The degassing system should be able to operate over the entire possible range of dialysate temperatures. When positioned downstream of the heater, the dialysate temperature in the degassing flow loop should be from about 35° C. to about 39.5° C. When positioned upstream of the heater, the possible temperature range of dialysate in the dialysate flow path can be larger, including from between about 10° C. to about 45° C.

The amount of gas removed by the degassing system is a function of the absolute headspace pressure in the degassing vessel 206, as well as the degassing flow loop flow rate. In some embodiments, the headspace pressure of the degassing vessel 206, an estimated degasser inlet carbon dioxide concentration is used, as described. In a preferred embodiment, the size and flow rate through the degassing flow loop and degas sprayer 207 is sufficient to ensure that dissolved gases in the liquid exiting the degassing vessel 206 through fluid line 204 are in approximate equilibrium with the gas partial pressure in the top portion 208, or headspace, of the degassing vessel 206. When the dissolved gases in the liquid are in approximate equilibrium with the gas partial pressure in the top portion 208 of the degassing vessel 206, the carbon dioxide pressure can be controlled by controlling the absolute headspace pressure. As such, the carbon dioxide pressure (dissolved $CO_2$ concentration) in the degassed dialysate flowing to the dialyzer can be controlled across a very wide range of inlet carbon dioxide pressures. The headspace pressure can be controlled to a predetermined target, irrespective of the estimated carbon dioxide concentration in the liquid entering the degassing vessel through dialysate line 201. In certain embodiments, the vacuum pump 218 is operated by the controller at a fixed rate. The absolute headspace pressure in the degassing vessel 206 is equal to the degassing vessel pressure as measured by gauge pressure sensor 216 plus the atmospheric pressure as measured by absolute ambient pressure sensor 222. Valves 219 and 223 can be selectively controlled by the controller to allow the vacuum pump 218 to remove air from the degassing vessel 206 or to allow air to flow into degassing vessel 206, thereby controlling the headspace pressure to the headspace pressure set point. In certain embodiments, the estimated degasser inlet carbon dioxide concentration can vary as a profile during a dialysis session, and as such, the headspace pressure set point can also vary during treatment. The degassing flow loop flow rate can be controlled by using a fixed pressure change to achieve a desired flow rate. The pressure change can be measured by the difference between the incoming fluid pressure as measured by pressure sensor 215 and the pressure within the degassing vessel 206 measured by gauge pressure sensor 216. Using the fixed pressure change, a pressure change set point can be set, and the fluid pressure at pressure sensor 215 varied by changing the fluid pump 213 rate until the pressure change set point is reached. In certain embodiments, the relationship between the pressure change and the flow rate can be empirically determined. Alternatively, the relationship can be calculated using an algorithm. The degassing flow loop flow rate should be set at a rate sufficient to ensure the dialysate comes into approximate equilibrium with the gas pressures in the degassing vessel 206, but low enough to avoid over degassing, erratic level behavior, or excess foam generation. In certain embodiments, the degassing flow loop flow rate can be set between 750 and 800 mL/min. Over degassing with a degassing flow loop flow rate of −800 mL/min and a dialysate flow rate of about 100 mL/min has not been observed. If the pump rate of fluid pump 213 deviates from the normal relationship with the pressure change, an obstruction in the fluid inlet 235 of the degassing vessel 206 or an error in the control over the pressure change may be indicated.

If an error is indicated, the system can generate an alert informing the user of the error and/or stop treatment. In certain embodiments, a protective system can be used. The protective system can receive the dialysate flow rate from a flow sensor (not shown) in the dialysate flow path and determine the change in pressure set point to operate the degassing flow loop flow rate at a set ratio to the dialysate flow path flow rate. The protective system can determine an expected operating rate (RPM) of the fluid pump 213 corresponding to the pressure change set point, and calculate a running average operating rate for fluid pump 213. The protective system can generate an alert if the running average of RPM for fluid pump 213 is outside of a predetermined range of the expected value. In certain embodiments, the predetermined range can be ±10% of the expected value. The protective system can also monitor the pressure in the headspace of the degassing vessel 206. The protective system can measure the ambient pressure with ambient pressure sensor 222 and the pressure inside the degassing vessel 206 with gauge pressure sensor 216 to calculate the absolute pressure within the degassing vessel 206 and can calculate a running average of the absolute pressure. The running average of absolute pressure can be compared to a predetermined limit, and an alert generated if the absolute pressure is outside of the predetermined limit.

Figure 14:
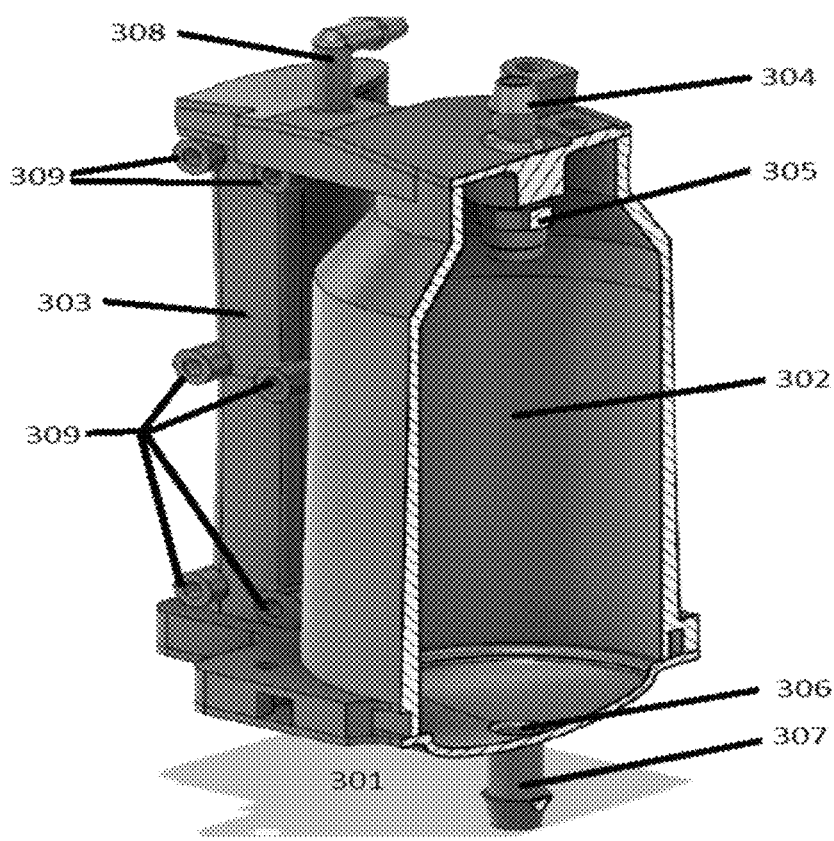
FIG. 14 shows a cross-sectional view of a degassing vessel.

FIG. 14 shows a cross section of a degassing vessel 301 for use in dialysis. The degassing vessel 301 can be divided into a spray chamber 302 and a float chamber 303. As described, the float chamber 303 can contain one or more level sensors in communication with a controller. In certain embodiments, the level sensors can be a magnetic float and a linear array of Hall effect sensors (not shown). Fluid enters the degassing vessel 301 through a fluid inlet 304 fluidly connected to a degas sprayer nozzle 305. The degas sprayer nozzle 305 sprays the fluid into the spray chamber 302. One or more channels (not shown) connect the spray chamber 302 to the float chamber 303 equilibrating the fluid level in each chamber. Degassed fluid exits the degassing vessel 301 through opening 306 fluidly connected to liquid outlet 307. In certain embodiments, the liquid outlet 307 is located in a bottom portion of the spray chamber 302. By placing the liquid outlet 307 at the bottom portion of the spray chamber 302, fluid may enter or exit the float chamber 303 only when the fluid level in the degassing vessel 301 is changing, reducing turbulence in the float chamber 303 and reducing the amount of gas bubbles that come out of solution in the float chamber 303. By reducing turbulence and gas bubbles in the float chamber 303, a more accurate and stable detection of fluid level may be achieved. Alternatively, the liquid outlet 307 can be positioned in a bottom portion of the float chamber 303 or between the spray chamber 302 and float chamber 303. Further, placing the liquid outlet 307 at the bottom portion of the spray chamber 302 increases the recirculating flow rate of fluid in the degassing flow loop, which beneficially increases the gas removal rate.

Gases can be removed from the degassing vessel 301 through gas outlet 308, which can be fluidly connected to a vacuum pump (not shown) by one or more valves. In a preferred embodiment, the gas outlet 308 is positioned at a top portion of the degassing vessel 301 between the spray chamber 302 and the float chamber 303. Placing the gas outlet 308 between the spray chamber 302 and float chamber 303 allows symmetrical gas removal from both chambers to maintain equal pressures in both chambers while preserving the filling, draining, and disinfection capabilities of the degassing vessel 301. Holes 309 can be included for securing a circuit board including the linear array of Hall effect sensors to detect the level of the float (not shown) and therefore the liquid level in the degassing vessel 301.

As illustrated in FIG. 14, the spray chamber 302 can have a substantially conical shape, as opposed to a tubular or other shape. The conical shape of the spray chamber 302 can cause spraying fluid to contact the walls of the spray chamber 302 at a shallower angle than if the spray chamber 302 has a tubular shape. The shallow angle of spray contacting the walls of the spray chamber 302 may result in less turbulence, reducing foaming of the fluid in the degassing vessel 301 and allowing more accurate measurements of the fluid level. The conical film of spray existing the degas sprayer nozzle 305 and impinging on the cone wall creates a foam cutting barrier above which the foam cannot grow. Reducing foaming also reduces gas flow restrictions out of the degassing vessel 301, allowing for a higher gas removal volume and faster headspace vacuum pressure recovery. When foam exits thru gas outlet 308 the foam can impede the gas flow thru the vacuum pump, causing an abrupt increase in headspace pressure. Preventing the foam from rising to gas outlet 308 prevents the gas flow from the vacuum pump from being restricted by the foam and the headspace can more quickly recover from any perturbation.

The spray chamber 302 can be any length and diameter sufficient to effectively capture bubbles in the fluid sprayed into the spray chamber 302. In certain embodiments, the spray chamber 302 can have a diameter of about 75 mm and a height of about 10 cm, which gives a balance of degassing capacity and foam control without excessive size or fluid volume. In other embodiments, the diameter can be from about 50 mm to about 100 mm, including between 50 mm and 75 mm, between 50 mm and 60 mm, between 60 mm and 100 mm, or between 75 mm and 100 mm. The height of the spray chamber 302 can be from about 60 mm and about 200 mm, including between 60 mm and 100 mm, between 60 mm and 75 mm, between 70 mm and 100 mm, between 90 mm and 125 mm, between 100 mm and 150 mm, between 125 mm and 200 mm or between 150 mm and 200 mm. A larger length and diameter of the spray chamber 302 can further reduce foaming by creating a better transition zone when fluid is sprayed into the spray chamber 302. A larger diameter spray chamber 302 also increases the surface area of the fluid and causes the sprayed liquid to have a greater contact time with the headspace, allowing more efficient gas removal.

In certain embodiments, the degas sprayer nozzle 305 can be constructed to create an even cone shaped spray, rather than a more coarse "fountain like" spray, which can further reduce foaming in the spray chamber 302. Importantly, by placing the degas sprayer at a top of the degassing vessel 301 rather than at a base of the degassing vessel 301, the sprayer can reduce foaming by acting as a cap to control the foam. A finer spray cone, rather than a fountain type spray, can also increase atomization of the fluid and accelerate gas removal, increasing the efficiency of the degasser.

Figure 15A:
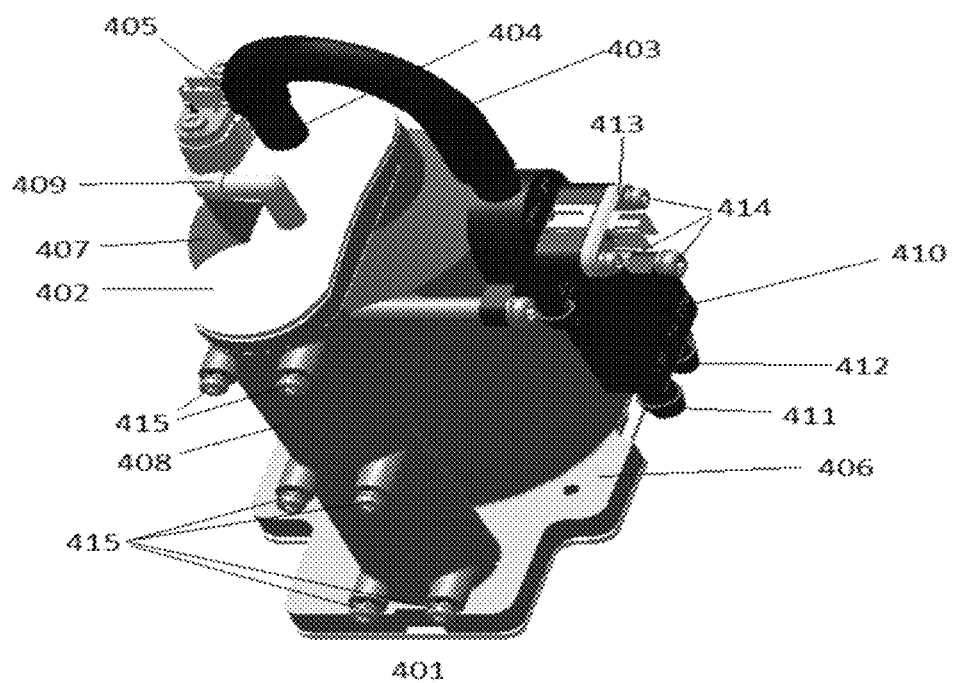
FIGS. 15A-B show top and side views of a degassing vessel.
Figure 15B:
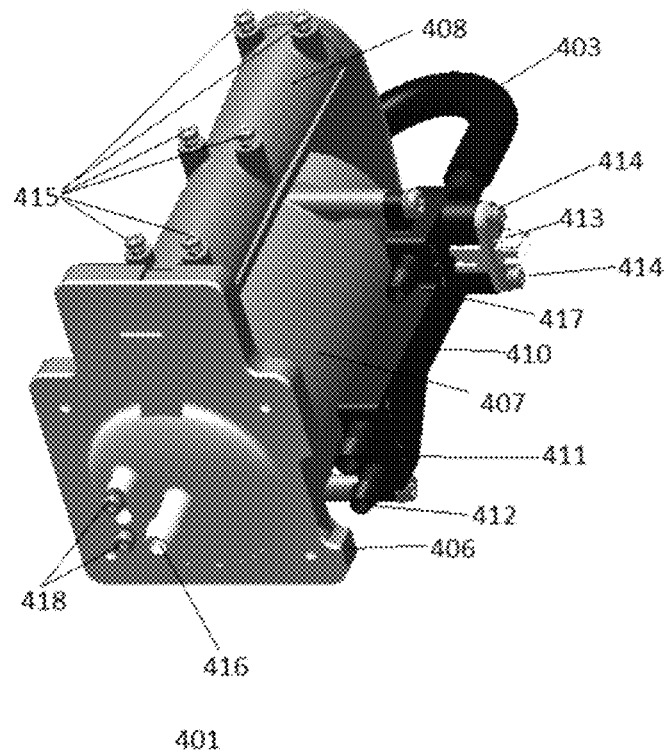

FIG. 15A is a top view of a degassing vessel 401 for use in dialysis and FIG. 15B is a side view of the degassing vessel 401. The degassing vessel 401 can include a spray chamber 407 and a float chamber 408. One or more level sensors (not shown) can be included in float chamber 408 to measure a fluid level in the degassing vessel 401. In certain embodiments, a manifold 410 can house fluid flow paths in a degassing flow loop. Fluid enters the manifold 410 from a dialysate flow path (not shown) through inlet 411. The fluid flows through fluid line 403 and fluid inlet 404 in a top portion 402 of the degassing vessel 401. The fluid inlet 404 can be fluidly connected to a degas sprayer (not shown in FIGS. 15A-B) in an interior of the spray chamber 407. Gases are removed via gas outlet 409, as illustrated in FIG. 15A, which can be fluidly connected to a vacuum pump (not shown). As illustrated in FIG. 15B, fluid exits the degassing vessel 401 through a liquid outlet 416 in a base 406 of the degassing vessel 401. Fluid lines (not shown) can connect the liquid outlet 416 to a fluid pump (not shown), and back to the manifold 410 through a second inlet 412 to recirculate the fluid in the degassing flow loop. Fluid can be directed back to a dialysate flow path, parallel to the degassing flow loop, through outlet 417 in manifold 410. Gauge pressure sensor 405 can measure the pressure in the headspace of the degassing vessel 401. Pressure sensor 413 can measure the pressure of the incoming liquid, which may be used to control the pump rates of the fluid pumps. Mounting bases 414, 415, and 418 can be included to attach the circuit board including the linear array of Hall effect sensors to detect the float in the float chamber 408.

Figure 16:
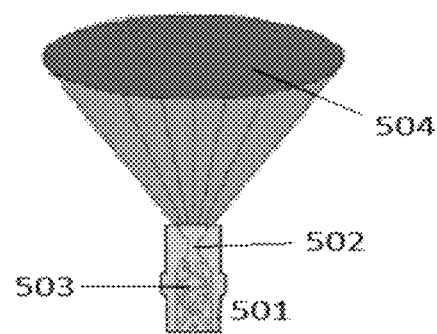
FIG. 16 shows a non-limiting embodiment of a spray nozzle for use in a degassing system.

As described, a cone-like spray from the degas sprayer reduces foaming in the degassing vessel. FIG. 16 illustrates a non-limiting embodiment of a spray nozzle 501 for use in a degassing system. The spray nozzle 501 includes an internal conduit 502 through which fluid flows. The internal conduit 502 can include one or more swirl inducing sets 503, which force the fluid into a vortex motion within the internal conduit 502, breaking the fluid apart. As a result, fluid exiting the spray nozzle 501 produces a full cone 504 that evenly distributes the spray pattern. The high surface area to volume ratio in the cone 504 allows gas to rapidly move from solution into equilibrium with the low gas pressure inside the degassing vessel. The spray nozzle 501 used with a degasser influences the relationship between the flow rate and the pressure change from the fluid inlet to the inside of the degassing vessel. As described, the relationship between the flow rate and pressure change can be used to control the degassing flow loop flow rate, and the pressure change set point can be adjusted based on the spray nozzle used. In a preferred embodiment, the spray is a dense conical film that smashes foam bubbles as the foam head grows upward, thus limiting the upward growth of the foam to the surface height defined by the spray cone.

Figure 17A:
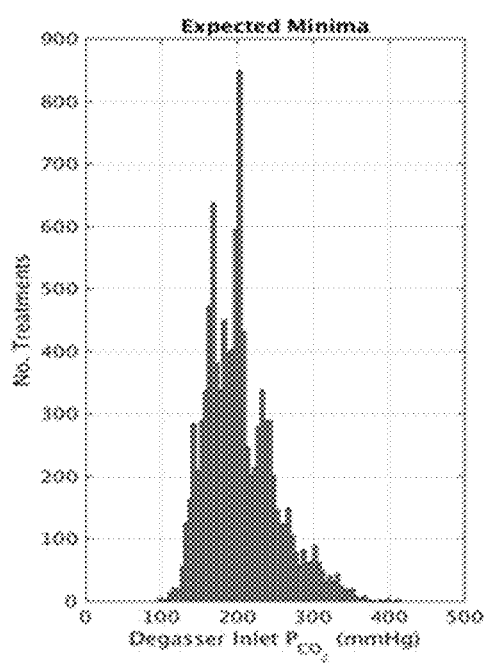
FIGS. 17A-B show expected carbon dioxide levels entering a degassing system based on simulated treatments.
Figure 17B:
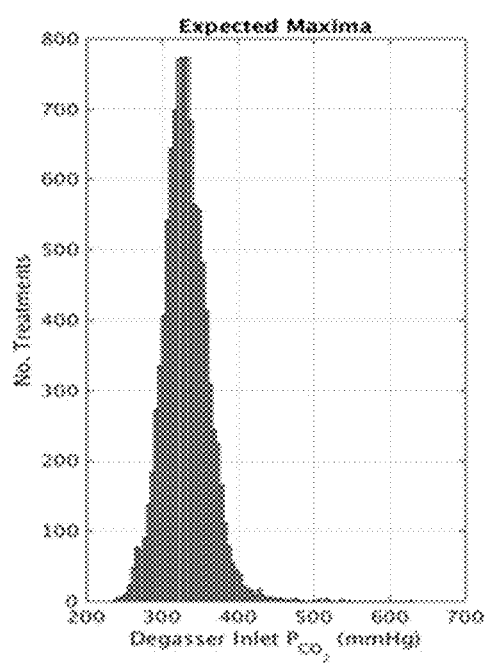

The degassing system should be able to control the carbon dioxide concentration in the dialysate flow path at the dialyzer inlet to a specified range, which in certain embodiments can be from 40 mmHg-150 mmHg $pCO_2$. The expected range of $CO_2$ concentrations at the inlet to the degassing flow loop can vary from between 85 to 650 mmHg $pCO_2$. To predict the expected degasser inlet $CO_2$ concentration, 10,000 simulated treatments were conducted. FIGS. 17A and 17B illustrate the expected $pCO_2$ minima and maxima, respectively. A summary of the simulations are shown in Table 1.

TABLE 1

Expected Sorbent Outlet PCO2 Level from Model

| Scenario | Minimum (mmHg) | Maximum (mmHg) | Range (mmHg) |
| --- | --- | --- | --- |
| 99$^{th}$ Percentile | 130 | 415 | 130-415 |
| 99.9$^{th}$ Percentile | 110 | 510 | 110-510 |
| 99.99$^{th}$ Percentile | 95 | 590 | 95-590 |
| 99.99$^{th}$ Percentile with Engineering Margin of 10% | 85 | 650 | 85-650 |

As illustrated in FIGS. 17A-B and Table 1, the 99$^{th}$ percentile for the minimum range for carbon dioxide concentration in dialysate exiting a sorbent cartridge, or the minimum range for carbon dioxide concentration in dialysate entering the degassing system is 130 mmHg. The 99.99$^{th}$ percentile for the minimum range for carbon dioxide concentration is 85 mmHg, even with a built-in engineering margin of 10%. The 99$^{th}$ percentile for the maximum range for carbon dioxide concentration is 415 mmHg. The 99.99$^{th}$ percentile for the maximum range for carbon dioxide concentration is 650 mmHg, even with a built-in engineering margin of 10%.

Fluid entering the degassing system will also contain dissolved nitrogen and oxygen gases. Table 2 summarizes the results of simulated treatments to determine the expected concentration ranges of oxygen and nitrogen when exiting the degasser as a function of the blood flow rate QB, the dialysate flow rate QD, the type of blood access, the dialyzer used, the dialyzer mass transfer—are coefficient of the dialyzer KoA, the initial patient nitrogen and oxygen blood concentrations CBin and the degasser inlet concentrations for both nitrogen and oxygen CDin. KoA is used as an approximation for the mass transfer coefficients of oxygen and nitrogen in the calculation to estimate the $O_2$ and $N_2$ concentrations in the dialysate exiting the dialyzer and returning to the degasser. The higher the KoA for the dialyzer, the higher the capability of the dialyzer membrane to transport molecular entities across the dialyzer membrane. The simulations provided the dialysance D, as well as the degasser outlet concentration for oxygen and nitrogen $C_{Dout}$. The data in Table 2 was obtained assuming that the concentration of nitrogen in the patient's blood was approximately equal to atmospheric nitrogen concentration, or 600 mmHg. A low blood oxygen concentration was assumed to be 30 mmHg, while a high blood oxygen concentration was assumed to be 100 mmHg. The dialysance of oxygen and nitrogen was approximated by the KoA for urea. Table 3 summarizes the findings for possible ranges of each gas in the dialysate based on high or low values for each gas.

TABLE 2

ENGINEERING ESTIMATES OF DIALYSATE pN2, pO2 @ DEGASSER INLET

| | Inputs | | | | | | | | | Outputs | |
|---|---|---|---|---|---|---|---|---|---|---|---|
| GAS CONTENT SCENARIO | QB (ml/min) | QD (ml/min) | Blood Access | Dialyzer Reference | ko (ml/min/m2) | A (m2) | CBin (mmHg) | CDin (mmHg) | | K or D (ml/min) | $C_{Dout}$ (mmHg) |
| Low N2 | 50 | 600 | CVC | Baxter CA50 | 262 | 0.5 | 600 | 4 | | 46 | 50 |
| Low O2 | 50 | 600 | CVC | Baxter CA50 | 262 | 0.5 | 30 | 1 | | 46 | 3 |
| Nominal Case N2 | 300 | 600 | Fistula | Baxter CA-HP 210 | 506 | 2.1 | 600 | 120 | | 272 | 338 |
| Nominal Case O2 | 300 | 600 | Fistula | Baxter CA-HP 210 | 506 | 2.1 | 90 | 20 | | 272 | 52 |
| High N2 | 500 | 499 | Fistula | B. Braun Xevonta Hi23 | 826 | 2.3 | 600 | 300 | | 396 | 538 |
| High O2 | 500 | 499 | Fistula | B. Braun Xevonta Hi23 | 826 | 2.3 | 100 | 50 | | 396 | 90 |

Note:
QB cannot equal QD
Assumptions
1 $pN_2$ in blood plasma is approximately equal to atmospheric nitrogen concentration (600 mmHg)
2 Low $pO_2$ in venous blood is assumed to be 30 mmHg.
3 High $pO_2$ in arterial blood is assumed to be 100 mmHg.
4 Dialysance of O2 and N2 can be approximated by KoA urea.

TABLE 3

Sorbent Outlet (Degasser Inlet) Gas Concentration Summary

| TEST CASE | pO2 (mmHg) | pN2 (mmHg) | pCO2 (mmHg) | % CO2 | Test Gas Mix |
|---|---|---|---|---|---|
| Low N2, Low O2, Low CO2 | 3 | 50 | 85 | 62% | 60% |
| Low N2, Low O2, High CO2 | 3 | 50 | 650 | 92% | 90% |
| Nominal N2, O2, CO2 | 52 | 338 | 300 | 43% | 40% |
| High N2, High O2, Low CO2 | 100 | 600 | 85 | 11% | 10% |
| High N2, High O2, High CO2 | 100 | 600 | 650 | 48% | 50% |

Table 3 summarizes the findings for possible ranges of each gas in the dialysate based on high or low values for each gas. As described, the possible ranges for carbon dioxide, nitrogen, and oxygen concentrations in the dialysate are used to control the degasser by setting a headspace pressure set point and degassing loop flow rate.

It will be apparent to one skilled in the art that various combinations and/or modifications and variations can be made in the dialysis system depending upon the specific needs for operation. Moreover, features illustrated or described as being part of an aspect of the invention can be included in the aspect of the invention, either alone or in combination.

We claim:

1. A system comprising:
a dialysate flow path comprising a degassing flow loop;
the degassing flow loop comprising a degassing vessel having a fluid inlet fluidly connected to a degas sprayer at a top portion of the degassing vessel, a liquid outlet at a bottom portion of the degassing vessel, and a gas outlet at a top portion of the degassing vessel;
a vacuum pump fluidly connected to the gas outlet;
a first fluid line fluidly connecting the liquid outlet to a second fluid line fluidly connected to the fluid inlet, the first fluid line comprising a fluid pump;
a third fluid line fluidly connecting the second fluid line to the dialysate flow path; and
a controller controlling the vacuum pump and the fluid pump.

2. The system of claim 1, wherein the degassing flow loop is parallel to the dialysate flow path; and wherein a flow rate of the degassing flow loop is controlled independently of a flow rate of the dialysate flow path.

3. The system of claim 1, further comprising a first pressure sensor in the degassing flow loop upstream of the fluid inlet and a second pressure sensor in the degassing flow loop in the gas outlet.

4. The system of claim 3, the controller controlling a first valve positioned between the vacuum pump and the gas outlet and/or a vent valve positioned between a vent and the gas outlet based on an absolute pressure in a headspace of the degassing vessel.

5. The system of claim 4, the controller controlling the first valve and/or the vent valve to maintain a carbon dioxide level in the third fluid line of between 40 mmHg and 150 mmHg pCO2.

6. The system of claim 1, further comprising at least one valve positioned in the third fluid line between the gas outlet and a vent.

7. The system of claim 1, further comprising an ambient pressure sensor.

8. The system of claim 1, wherein the degassing vessel comprises a level sensor in communication with the controller; the level sensor comprising one or more of: a float with a magnet and a linear array of Hall effect sensors, an ultrasonic sensor, and a capacitive sensor.

* * * * *